US006733521B2

(12) United States Patent
Chobotov et al.

(10) Patent No.: US 6,733,521 B2
(45) Date of Patent: May 11, 2004

(54) DELIVERY SYSTEM AND METHOD FOR ENDOVASCULAR GRAFT

(75) Inventors: Michael V. Chobotov, Santa Rosa, CA (US); Brian A. Glynn, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 27 days.

(21) Appl. No.: 09/834,278

(22) Filed: Apr. 11, 2001

(65) Prior Publication Data

US 2002/0151956 A1 Oct. 17, 2002

(51) Int. Cl.[7] ................................................ A61F 2/06
(52) U.S. Cl. ...................................... 623/1.12; 606/108
(58) Field of Search ............................... 623/1.11, 1.12; 606/108

(56) References Cited

U.S. PATENT DOCUMENTS

| | | | |
|---|---|---|---|
| 4,140,126 A | 2/1979 | Choudhury | 128/325 |
| 4,562,596 A | 1/1986 | Kornberg | 623/1 |
| 4,580,568 A | 4/1986 | Gianturco | 128/345 |
| 4,787,899 A | 11/1988 | Lazarus | 623/1 |
| 5,104,399 A | 4/1992 | Lazarus | 623/1 |
| 5,151,105 A | 9/1992 | Kwan-Gett | 623/1 |
| 5,156,620 A | 10/1992 | Pigott | 623/1 |
| 5,360,443 A | 11/1994 | Barone et al. | 623/1 |
| 5,387,235 A | 2/1995 | Chuter | 623/1 |
| 5,397,345 A | 3/1995 | Lazarus | 623/1 |
| 5,456,694 A | 10/1995 | Marin et al. | 606/198 |
| 5,456,713 A | 10/1995 | Chuter | 623/1 |
| 5,464,449 A | 11/1995 | Ryan et al. | 623/1 |
| 5,480,423 A | 1/1996 | Ravenscroft et al. | 623/1 |
| 5,489,295 A | 2/1996 | Piplani et al. | 623/1 |
| 5,522,880 A | 6/1996 | Barone et al. | |
| 5,522,883 A | 6/1996 | Slater et al. | |
| 5,562,724 A | 10/1996 | Vorwerk et al. | |
| 5,562,726 A | 10/1996 | Chuter | 623/1 |
| 5,578,071 A | 11/1996 | Parodi et al. | 623/1 |
| 5,578,072 A | 11/1996 | Barone et al. | |
| 5,609,625 A | 3/1997 | Piplani et al. | |
| 5,628,783 A | 5/1997 | Quiachon et al. | 623/1 |

(List continued on next page.)

FOREIGN PATENT DOCUMENTS

| | | |
|---|---|---|
| EP | 0 943 302 A2 | 9/1999 |
| EP | 1 093 772 A2 | 4/2001 |
| EP | 0 808 140 B1 | 12/2001 |

(List continued on next page.)

OTHER PUBLICATIONS

US 6,413,270, 7/2002, Thornton et al. (withdrawn)
AneuRX stent graft brochure, An Innovative Modular Approach For The Treatment Of Abdominal Aortic Aneurysms (AAA), *Medtronic*.

(List continued on next page.)

*Primary Examiner*—Corrine McDermott
*Assistant Examiner*—Thomas Sweet
(74) *Attorney, Agent, or Firm*—Townsend and Townsend and Crew LLP

(57) ABSTRACT

A flexible low profile delivery system for delivery of an expandable intracorporeal device, specifically, an endovascular graft, which has at least one belt circumferentially disposed about the device in a constraining configuration. The belt is released by a release member, such as a release wire, by retracting the wire from looped ends of the belt. Multiple belts can be used and can be released sequentially so as to control the order of release and placement of the endovascular graft. An outer protective sheath may be disposed about the endovascular graft while in a constrained state which must first be retracted or otherwise removed prior to release of the graft from a constrained state. The delivery system can be configured for delivery over a guiding device such as a guidewire.

25 Claims, 17 Drawing Sheets

U.S. PATENT DOCUMENTS

| | | |
|---|---|---|
| 5,632,772 A | 5/1997 | Alcime et al. ................. 623/1 |
| 5,639,278 A | 6/1997 | Dereume et al. .............. 623/1 |
| 5,662,675 A | 9/1997 | Polanskyj Stockert et al. |
| 5,662,700 A | 9/1997 | Lazarus ........................ 623/1 |
| 5,665,115 A | 9/1997 | Cragg ........................... 623/1 |
| 5,669,936 A | 9/1997 | Lazarus ........................ 623/1 |
| 5,676,671 A | 10/1997 | Inoue ........................ 606/108 |
| 5,676,696 A | 10/1997 | Marcade ....................... 623/1 |
| 5,676,697 A | 10/1997 | McDonald ..................... 623/1 |
| 5,683,449 A | 11/1997 | Marcade ....................... 623/1 |
| 5,683,451 A | 11/1997 | Lenker et al. ................. 623/1 |
| 5,693,083 A | 12/1997 | Baker et al. ................... 623/1 |
| 5,693,084 A | 12/1997 | Chuter .......................... 623/1 |
| 5,693,088 A | 12/1997 | Lazarus ........................ 623/1 |
| 5,709,701 A | 1/1998 | Parodi ....................... 606/194 |
| 5,709,703 A | 1/1998 | Lukic et al. ................ 606/198 |
| 5,720,776 A | 2/1998 | Chuter et al. ................. 623/1 |
| 5,723,004 A | 3/1998 | Dereume et al. .............. 623/1 |
| 5,733,325 A | 3/1998 | Robinson et al. ............. 623/1 |
| 5,749,920 A | 5/1998 | Quiachon et al. ............. 623/1 |
| 5,749,921 A | 5/1998 | Lenker et al. ................. 623/1 |
| 5,769,885 A | 6/1998 | Quichon et al. |
| 5,769,887 A | 6/1998 | Brown et al. .................. 623/1 |
| 5,782,838 A * | 7/1998 | Beyar et al. ............... 623/1.11 |
| 5,782,909 A | 7/1998 | Quichon et al. |
| 5,800,518 A | 9/1998 | Piplani et al. |
| 5,824,039 A | 10/1998 | Piplani et al. |
| 5,824,041 A | 10/1998 | Lenker et al. ................. 623/1 |
| 5,824,058 A | 10/1998 | Ravenscroft et al. .......... 623/1 |
| 5,843,158 A | 12/1998 | Lenker et al. ................. 623/1 |
| 5,843,162 A * | 12/1998 | Inoue ........................ 623/1.13 |
| 5,843,167 A | 12/1998 | Dwyer et al. .................. 623/1 |
| 5,855,598 A | 1/1999 | Pinchuk ........................ 623/1 |
| 5,871,536 A | 2/1999 | Lazarus et al. ................ 623/1 |
| 5,873,906 A | 2/1999 | Lau et al. |
| 5,906,619 A | 5/1999 | Olson et al. ................. 606/108 |
| 5,919,204 A | 7/1999 | Lukic et al. ................ 606/198 |
| 5,944,750 A | 8/1999 | Tanner et al. .................. 623/1 |
| 5,954,729 A | 9/1999 | Bachmann et al. ......... 606/108 |
| 5,957,973 A | 9/1999 | Quiachon et al. |
| 5,968,068 A | 10/1999 | Dehdashtian et al. ....... 606/192 |
| 5,972,023 A | 10/1999 | Tanner et al. ............... 606/219 |
| 5,976,179 A | 11/1999 | Inoue ............................ 623/1 |
| 5,976,650 A | 11/1999 | Campbell et al. |
| 5,984,964 A | 11/1999 | Roberts et al. ................ 623/12 |
| 5,993,481 A | 11/1999 | Marcade et al. ............... 623/1 |
| 6,001,123 A | 12/1999 | Lau |
| 6,004,347 A | 12/1999 | McNamara et al. ........... 623/1 |
| 6,004,348 A | 12/1999 | Banas et al. |
| 6,017,364 A | 1/2000 | Lazarus |
| 6,019,778 A | 2/2000 | Wilson et al. .............. 606/198 |
| 6,019,779 A * | 2/2000 | Thorud et al. .............. 606/198 |
| 6,024,763 A | 2/2000 | Lenker et al. ................. 623/1 |
| 6,030,414 A | 2/2000 | Taheri ........................... 623/1 |
| 6,036,413 A | 3/2000 | Chandrasekar .............. 409/231 |
| 6,036,723 A | 3/2000 | Anidjar et al. ................. 623/1 |
| 6,036,725 A | 3/2000 | Avellanet ....................... 623/1 |
| 6,039,758 A | 3/2000 | Quiachon et al. ............. 623/1 |
| 6,042,589 A | 3/2000 | Marianne .................... 606/108 |
| 6,042,605 A | 3/2000 | Martin et al. .................. 623/1 |
| 6,045,557 A | 4/2000 | White et al. ................. 606/108 |
| 6,051,020 A | 4/2000 | Goicoechea et al. ........... 623/1 |
| 6,059,821 A | 5/2000 | Auidjar et al. ................. 623/1 |
| 6,070,589 A | 6/2000 | Keith et al. ................. 128/898 |
| 6,077,297 A | 6/2000 | Robinson et al. .......... 623/1.11 |
| 6,098,630 A | 8/2000 | Papazoglou |
| 6,110,198 A | 8/2000 | Fogarty et al. ............ 623/1.12 |
| 6,126,685 A | 10/2000 | Lenker et al. ................. 623/1 |
| 6,132,459 A | 10/2000 | Piplani et al. ............. 623/1.13 |
| 6,139,572 A | 10/2000 | Campbell et al. |
| 6,146,389 A | 11/2000 | Geitz .......................... 606/108 |
| 6,156,063 A | 12/2000 | Douglas .................... 623/1.12 |
| 6,165,210 A | 12/2000 | Lau et al. ................... 623/1.12 |
| 6,165,213 A | 12/2000 | Goicoechea et al. ....... 623/1.34 |
| 6,168,610 B1 | 1/2001 | Marin et al. ................ 606/198 |
| 6,168,616 B1 | 1/2001 | Brown, III ................. 623/1.11 |
| 6,168,617 B1 | 1/2001 | Blaeser et al. ............. 623/1.11 |
| 6,168,618 B1 * | 1/2001 | Frantzen .................... 623/1.12 |
| 6,168,620 B1 | 1/2001 | Kerr ........................... 623/1.13 |
| 6,183,481 B1 | 2/2001 | Lee et al. .................... 606/108 |
| 6,183,504 B1 | 2/2001 | Inoue ......................... 623/1.11 |
| 6,187,036 B1 | 2/2001 | Shaolian et al. |
| 6,193,745 B1 | 2/2001 | Fogarty et al. ............ 623/1.12 |
| 6,197,046 B1 | 3/2001 | Piplani et al. |
| 6,197,049 B1 | 3/2001 | Shaolian et al. |
| 6,200,339 B1 | 3/2001 | Leschinsky et al. ....... 623/1.35 |
| 6,203,550 B1 | 3/2001 | Olson ......................... 606/108 |
| 6,203,568 B1 | 3/2001 | Lombardi et al. |
| 6,210,422 B1 | 4/2001 | Douglas ..................... 606/194 |
| 6,210,434 B1 | 4/2001 | Quiachon et al. |
| 6,210,435 B1 | 4/2001 | Piplani et al. .............. 623/1.35 |
| 6,214,038 B1 | 4/2001 | Piplani et al. .............. 623/1.11 |
| 6,224,609 B1 | 5/2001 | Ressemann et al. |
| 6,235,050 B1 | 5/2001 | Quiachon et al. |
| 6,235,051 B1 | 5/2001 | Murphy ..................... 623/1.12 |
| 6,241,759 B1 | 6/2001 | Piplani et al. |
| 6,261,316 B1 | 7/2001 | Shaolian et al. ........... 623/1.11 |
| 6,261,317 B1 | 7/2001 | Inoue |
| 6,264,662 B1 | 7/2001 | Lauterjung |
| 6,280,466 B1 | 8/2001 | Kugler et al. .............. 623/1.12 |
| 6,283,991 B1 | 9/2001 | Cox et al. ................... 623/1.13 |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,293,969 B1 | 9/2001 | Chuter |
| 6,302,891 B1 * | 10/2001 | Nadal ......................... 606/108 |
| 6,302,906 B1 | 10/2001 | Goicoechea et al. |
| 6,302,908 B1 | 10/2001 | Parodi et al. .............. 623/1.31 |
| 6,306,145 B1 | 10/2001 | Leschinsky |
| 6,312,462 B1 | 11/2001 | McDermott et al. ....... 623/1.25 |
| 6,322,587 B1 | 11/2001 | Quiachon et al. |
| 6,325,819 B1 | 12/2001 | Pavcnik et al. |
| 6,325,825 B1 | 12/2001 | Kula et al. |
| 6,331,186 B1 | 12/2001 | Wang et al. |
| 6,331,190 B1 | 12/2001 | Shokoohi et al. |
| 6,344,044 B1 | 2/2002 | Fulkerson et al. |
| 6,344,054 B1 | 2/2002 | Parodi |
| 6,352,553 B1 | 3/2002 | van der Burg et al. .... 623/1.23 |
| 6,352,561 B1 | 3/2002 | Leopold et al. ............ 623/1.23 |
| 6,371,979 B1 * | 4/2002 | Beyar et al. ................ 623/1.12 |
| 6,416,536 B1 | 7/2002 | Yee |
| 6,425,898 B1 | 7/2002 | Wilson et al. |
| 6,428,566 B1 | 8/2002 | Holt |
| 6,428,567 B2 | 8/2002 | Wilson et al. |
| 6,432,129 B2 | 8/2002 | DiCaprio |
| 6,432,131 B1 | 8/2002 | Ravenscroft |
| 6,436,104 B2 | 8/2002 | Hojeibane |
| 6,443,979 B1 | 9/2002 | Stalker et al. |
| 6,447,501 B1 | 9/2002 | Solar et al. |
| 6,447,522 B2 | 9/2002 | Gambale et al. |
| 6,451,053 B1 | 9/2002 | Dehdashtian et al. |
| 6,471,718 B1 | 10/2002 | Staehle et al. |
| 6,471,722 B1 | 10/2002 | Inoue |
| 6,475,166 B1 | 11/2002 | Escano |
| 6,475,208 B2 | 11/2002 | Mauch |
| 6,478,807 B1 | 11/2002 | Foreman et al. |
| 6,485,515 B2 | 11/2002 | Strecker |
| 6,500,202 B1 | 12/2002 | Shaolian et al. |
| 6,517,574 B1 | 2/2003 | Chuter |
| 6,520,983 B1 | 2/2003 | Colgan et al. |
| 6,520,984 B1 | 2/2003 | Garrison et al. |

| | | |
|---|---|---|
| 6,530,947 B1 | 3/2003 | Euteneuer et al. |
| 6,533,806 B1 | 3/2003 | Sullivan et al. |
| 6,533,807 B2 | 3/2003 | Wolinsky et al. |
| 6,533,811 B1 | 3/2003 | Ryan et al. |
| 6,540,778 B1 | 4/2003 | Quiachon et al. |
| 6,554,858 B2 | 4/2003 | Dereume et al. |
| 6,562,063 B1 | 5/2003 | Euteneuer et al. |
| 2001/0004706 A1 | 6/2001 | Hojeibane |
| 2001/0007954 A1 | 7/2001 | Shaolian et al. |
| 2001/0012943 A1 | 8/2001 | Shaolian et al. |
| 2001/0014823 A1 | 8/2001 | Ressemann et al. |
| 2001/0020184 A1 | 9/2001 | Dehdashtain et al. ...... 623/1.16 |
| 2001/0037142 A1 | 11/2001 | Stelter et al. |
| 2001/0047150 A1 | 11/2001 | Chobotov |
| 2001/0049534 A1 | 12/2001 | Lachat |
| 2002/0077692 A1 | 6/2002 | Besselink |
| 2002/0099405 A1 | 7/2002 | Yurek et al. |
| 2002/0099431 A1 | 7/2002 | Armstrong et al. |
| 2002/0099433 A1 | 7/2002 | Fischell et al. |
| 2002/0099435 A1 | 7/2002 | Stinson |
| 2002/0099437 A1 | 7/2002 | Anson et al. |
| 2002/0103525 A1 | 8/2002 | Cummings |
| 2002/0111633 A1 | 8/2002 | Stoltze et al. |
| 2002/0111666 A1 | 8/2002 | Hart et al. |
| 2002/0111675 A1 | 8/2002 | Wilson |
| 2002/0116046 A1 | 8/2002 | DiCaprio et al. |
| 2002/0116047 A1 | 8/2002 | Vardi et al. |
| 2002/0120321 A1 | 8/2002 | Gunderson et al. |
| 2002/0123794 A1 | 9/2002 | Ellis et al. |
| 2002/0138081 A1 | 9/2002 | Blaeser et al. |
| 2002/0138127 A1 | 9/2002 | Stiger et al. |
| 2002/0138128 A1 | 9/2002 | Stiger et al. |
| 2002/0143381 A1 | 10/2002 | Gilligan et al. |
| 2002/0143383 A1 | 10/2002 | Parodi |
| 2002/0143387 A1 | 10/2002 | Soetikno et al. |
| 2002/0156489 A1 | 10/2002 | Gellman et al. |
| 2002/0165602 A1 | 11/2002 | Douglas et al. |
| 2002/0177890 A1 | 11/2002 | Lenker |
| 2002/0183832 A1 | 12/2002 | Penn et al. |
| 2002/0188341 A1 | 12/2002 | Elliott |
| 2002/0193867 A1 | 12/2002 | Gladdish, Jr. et al. |
| 2002/0198588 A1 | 12/2002 | Armstrong et al. |
| 2003/0009211 A1 | 1/2003 | DiCarlo |
| 2003/0009212 A1 | 1/2003 | Kerr |
| 2003/0014101 A1 | 1/2003 | Harrison |
| 2003/0050684 A1 | 3/2003 | Abrams et al. |
| 2003/0050686 A1 | 3/2003 | Raeder-Devens et al. |
| 2003/0074048 A1 | 4/2003 | Sherry |
| 2003/0074050 A1 | 4/2003 | Kerr |

FOREIGN PATENT DOCUMENTS

| | | |
|---|---|---|
| EP | 1212988 | 6/2002 |
| EP | 1212989 | 6/2002 |
| WO | WO 96/24308 A1 | 8/1996 |
| WO | WO 98/06355 | 2/1998 |
| WO | WO 98/41167 | 9/1998 |
| WO | WO 99/11199 A1 | 3/1999 |
| WO | WO 00/13613 A1 | 3/2000 |
| WO | WO 00/33769 | 6/2000 |
| WO | 00/42947 | 7/2000 |
| WO | 00/42948 | 7/2000 |
| WO | WO 01/58387 A1 | 8/2001 |
| WO | WO 01/67993 A2 | 9/2001 |
| WO | WO 01/74270 A2 | 10/2001 |
| WO | 02/056798 | 7/2002 |
| WO | 02/060345 | 8/2002 |
| WO | 03/022181 | 3/2003 |

OTHER PUBLICATIONS

Lawrence, Jr. et al., "Percutaneous Endovascular Graft: Experimental Evaluation", *Radiology,* 163/2:357–360 (1987).

Mirich et al., "Percutaneously Placed Endovascular Grafts for Aortic Aneurysms: Feasibility Study", *Radiology,* 170/3:1033–1037 (1989).

* cited by examiner

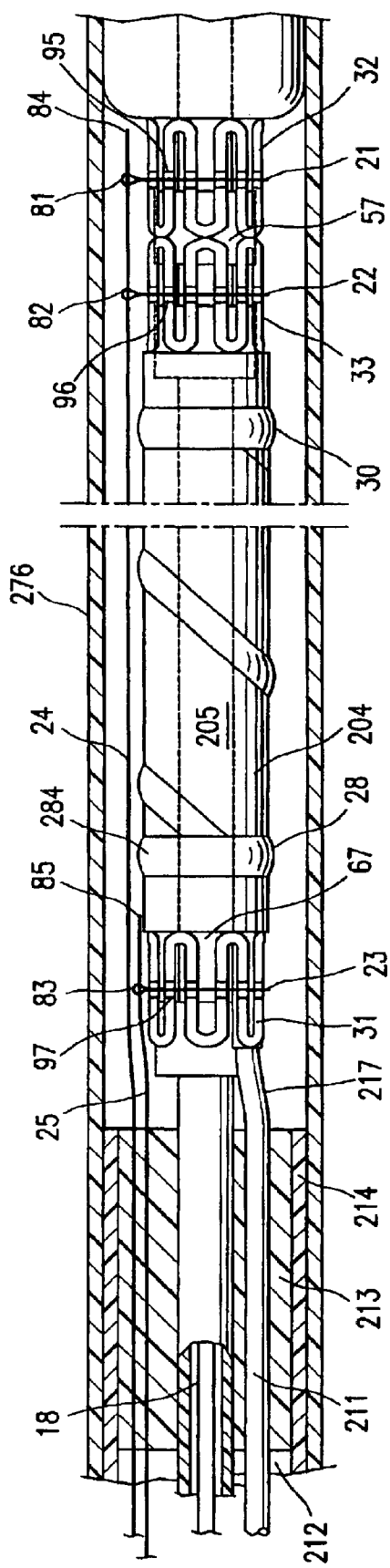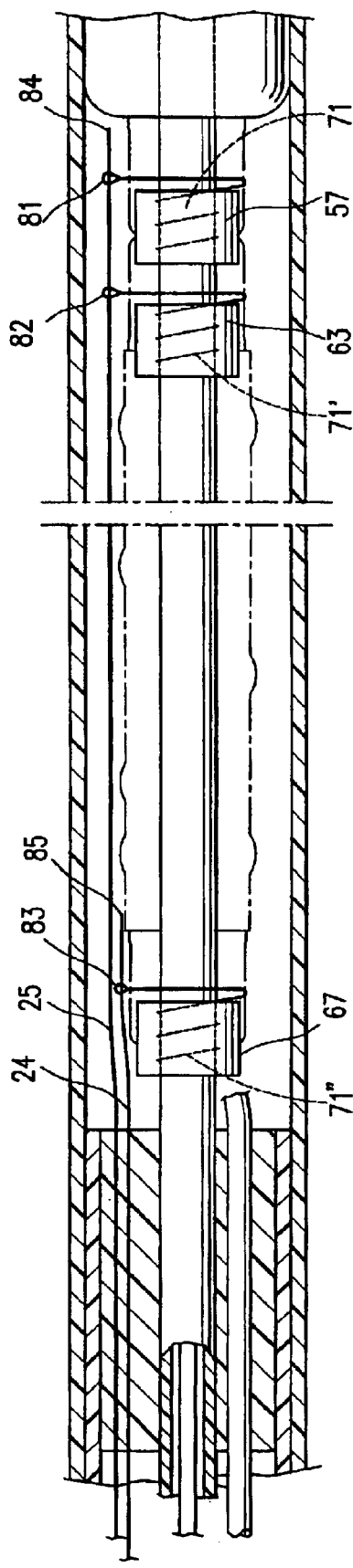
FIG. 6A
FIG. 6B

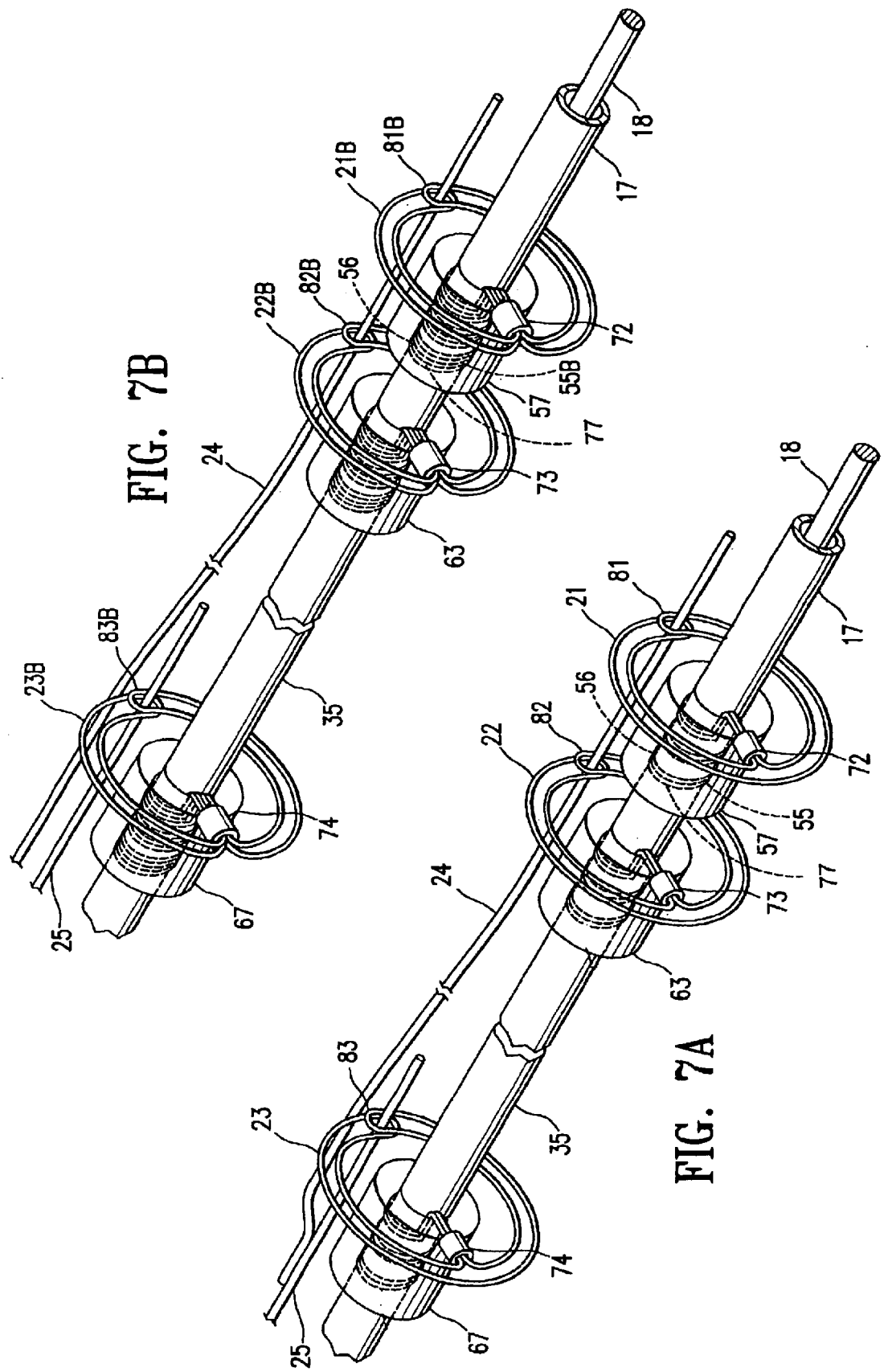

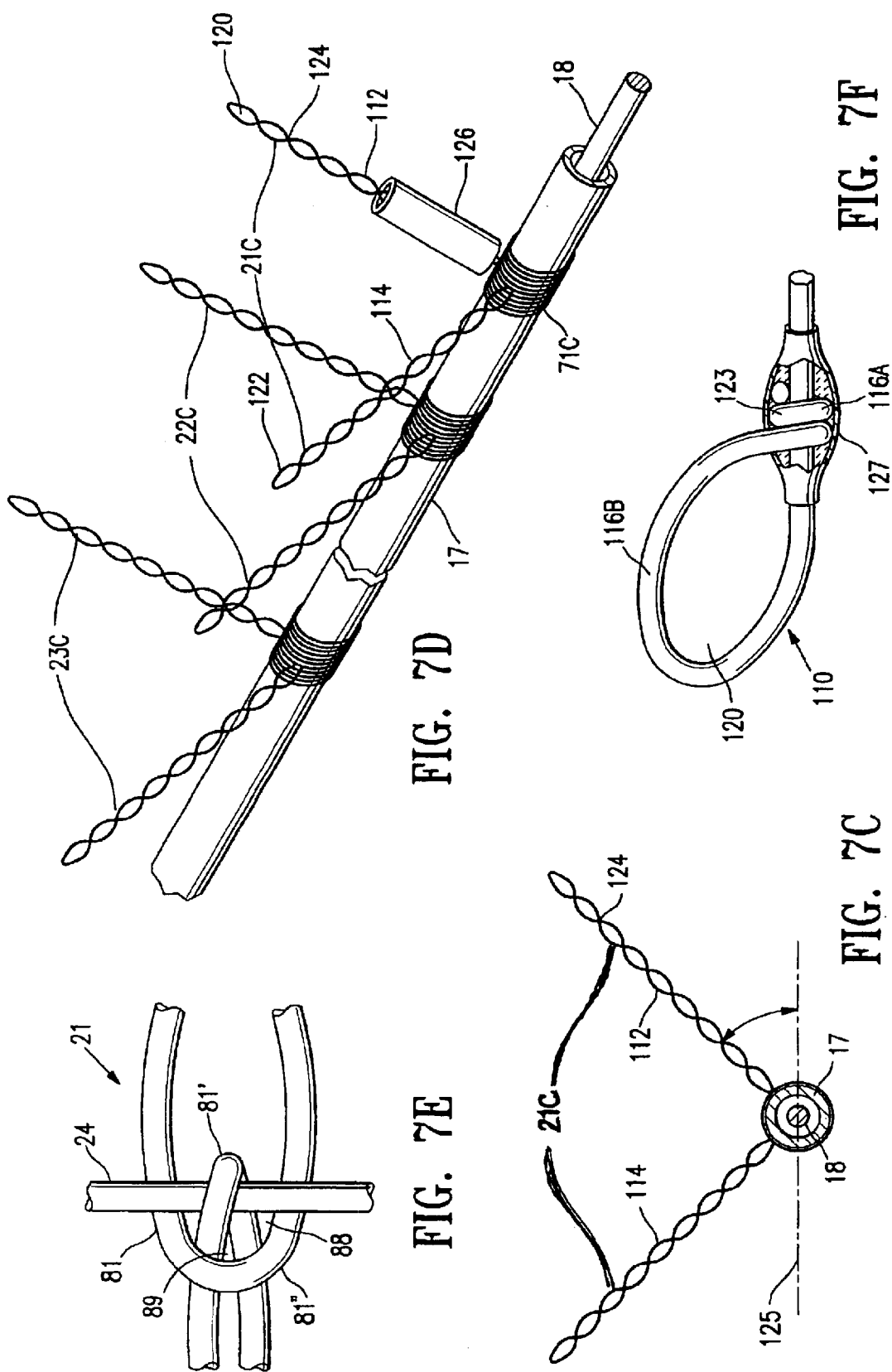

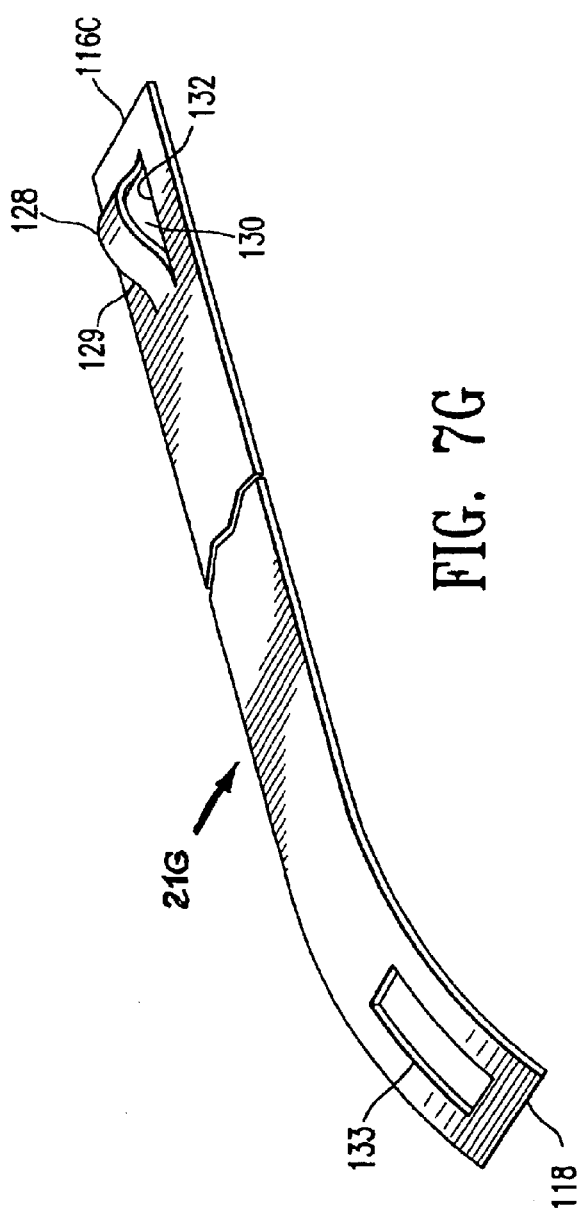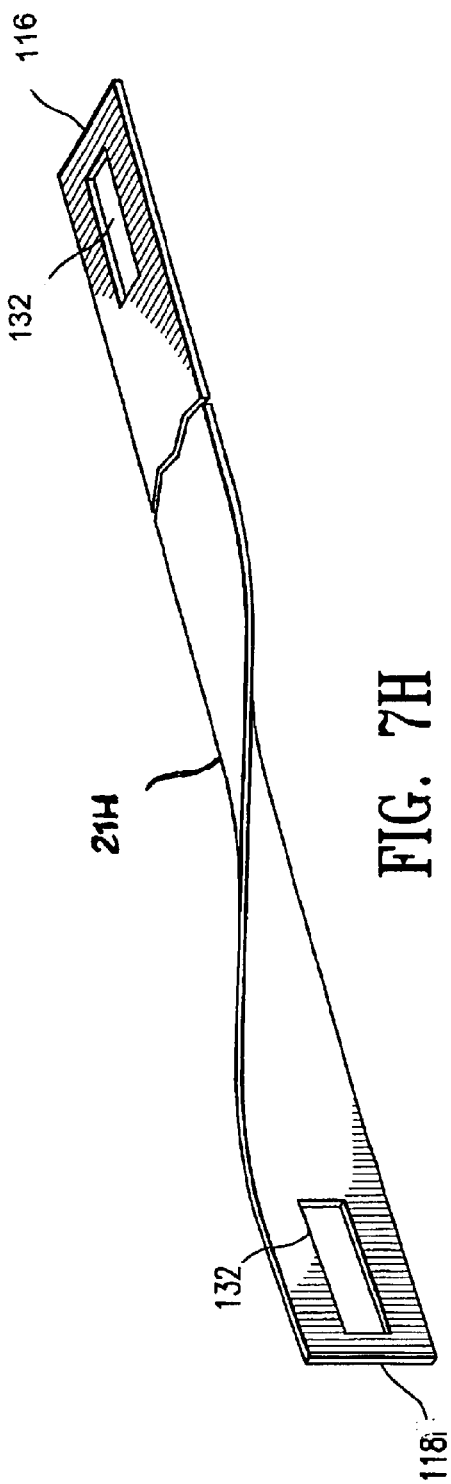

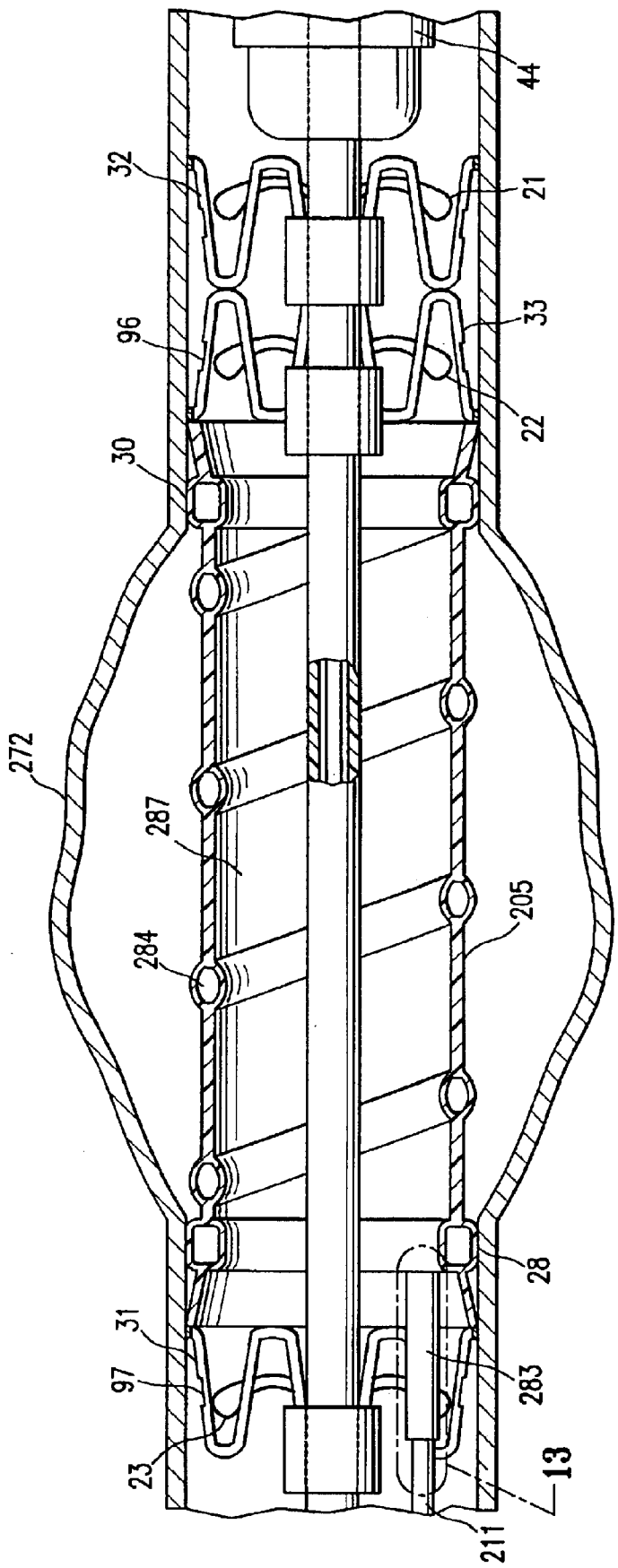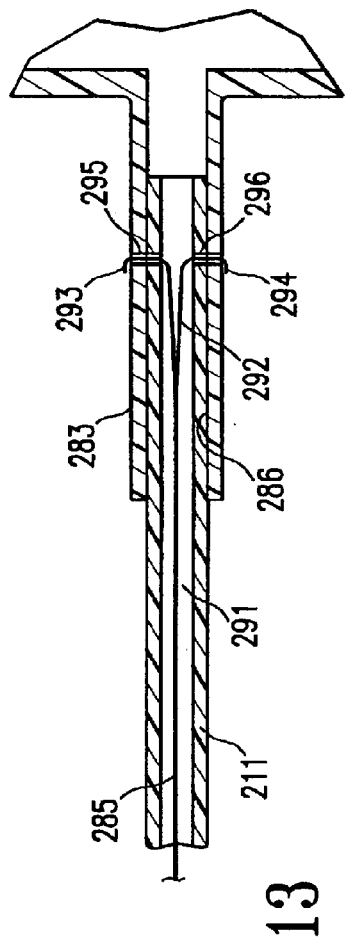
FIG. 12
FIG. 13

DELIVERY SYSTEM AND METHOD FOR ENDOVASCULAR GRAFT

BACKGROUND

The present invention relates to a system and method for the treatment of disorders of the vasculature. More specifically, the present invention relates to a system and method for treatment of thoracic or abdominal aortic aneurysm and the like, which is a condition manifested by expansion and weakening of the aorta. Such conditions require intervention due to the severity of the sequelae, which can be death. Prior methods of treating aortic aneurysm have consisted of invasive surgical methods with graft placement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures can have a high mortality rate due to the possibility of the rupture discussed above in addition to other factors. Such other factors for surgical treatment of aortic aneurysms can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W. B. Saunders Company.

Due to the inherent risks and complexities of surgical procedures, various attempts have been made in the development of alternative methods for deployment of grafts within aortic aneurysms. One such method is the non-invasive technique of percutaneous delivery by a catheter-based system. Such a method is described in Lawrence, Jr. et al. in "Percutaneous Endovascular Graft: Experimental Evaluation", *Radiology* (May 1987). Lawrence described therein the use of a Gianturco stent as disclosed in U.S. Pat. No. 4,580,568. The stent is used to position a Dacron fabric graft within the vessel. The Dacron graft is compressed within the catheter and then deployed within the vessel to be treated. A similar procedure has also been described by Mirich et al. in "Percutaneously Placed Endovascular Grafts for Aortic Aneurysms: Feasibility Study", *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery systems used to deliver the grafts are relatively large in profile, often up to 24 French, and stiff in longitudinal bending. The large profile and relatively high bending stiffness of existing delivery systems makes delivery through the vessels of a patient difficult and can pose the risk of dissection or other trauma to the patient's vessels. In particular, the iliac arteries of a patient are often too narrow or irregular for the passage of existing percutaneous devices. Because of this, non-invasive percutaneous graft delivery for treatment of aortic aneurysm is contraindicated for many patients who would otherwise benefit from it.

What is needed is an endovascular graft and delivery system having a small outer diameter relative to existing systems and high flexibility to facilitate percutaneous delivery in patients who require such treatment. What is also needed is a delivery system for an endovascular graft that is simple, reliable and that can accurately and safely deploy an endovascular graft within a patient's body, lumen or vessel.

SUMMARY

The invention is directed generally to a delivery system for delivery of an expandable intracorporeal device, specifically, an endovascular graft. Embodiments of the invention are directed to percutaneous non-invasive delivery of endovascular grafts which eliminate the need for a surgical cut-down in order to access the afflicted artery or other intracorporeal conduit of the patient being treated. Such a non-invasive delivery system and method result in shorter procedure duration, expedited recovery times and lower risk of complication. The flexible low profile properties of some embodiments of the invention also make percutaneous non-invasive procedures for delivery of endovascular grafts available to patient populations that may not otherwise have such treatment available. For example, patients with small anatomies or particularly tortuous vasculature may be contraindicated for procedures that involve the use of delivery systems that do not have the flexible or low profile characteristics of embodiments of the present invention.

In one embodiment, the delivery system has an elongate shaft with a proximal section and a distal section. The distal section of the elongate shaft includes a portion having an expandable intracorporeal device. An elongate belt support member is disposed adjacent a portion of the expandable intracorporeal device and a belt is secured to the belt support member and circumferentially disposed about the expandable intracorporeal device. The belt member constrains at least a portion of the expandable intracorporeal device. A release member releasably secures the belt in the constraining configuration.

Another embodiment of the invention is a delivery system that has an elongate shaft with a proximal section and a distal section. The distal section of the elongate shaft has an elongate belt support member disposed adjacent a portion of the expandable intracorporeal device. A belt is secured to the belt support member and is circumferentially disposed about the expandable intracorporeal device. The belt has a configuration which constrains the expandable intracorporeal device and a release member releasably secures the belt in the constraining configuration. The belt may constrain any portion of the expandable intracorporeal device, such as a self-expanding portion of the expandable intracorporeal device. A self-expanding portion of the device may include a self-expanding member such as a tubular stent.

In a particular embodiment of the invention, a plurality of belts are secured to various axial positions on the belt support member, are circumferentially disposed about the expandable intracorporeal device and have a configuration which constrains the expandable intracorporeal device. At least one release member releasably secures the belts in the constraining configuration. Each belt can be released by a single separate release member which engages each belt separately, or multiple belts can be released by a single release member. The order in which the belts are released can be determined by the axial position of the belts and the direction of movement of the release member.

Another embodiment of the invention is directed to a delivery system for delivery of a self-expanding endovascular graft with a flexible tubular body portion and at least one self-expanding member secured to an end of the endovascular graft. The delivery system has an elongate shaft having a proximal section and a distal section. The distal section of the elongate shaft has an elongate belt support member disposed within the self-expanding member of the endovascular graft and a belt which is secured to the belt support member adjacent the self-expanding member. The belt is also circumferentially disposed about the self-expanding member and has a configuration which constrains the self-expanding member. A release wire releasably secures ends of the belt in the constraining configuration.

A further embodiment of the invention includes a delivery system for delivery of an endovascular graft with a flexible tubular body portion and a plurality of self-expanding members secured to ends of the endovascular graft. The delivery system has an elongate shaft with a proximal section and a distal section. The distal section of the elongate shaft has an elongate guidewire tube disposed within the endovascular graft in a constrained state. A plurality of shape memory thin wire belts are secured to the guidewire tube respectively adjacent the self-expanding members. The belts are circumferentially disposed about the respective self-expanding members and have a configuration which constrains the respective self-expanding members. A first release wire releasably secures ends of the belts disposed about the self-expanding members at the proximal end of the endovascular graft in a constraining configuration. A second release wire releasably secures ends of the belts disposed about the self-expanding members at a distal end of the endovascular graft in the constraining configuration.

The invention also is directed to a method for deploying an expandable intracorporeal device within a patient's body. The method includes providing a delivery system for delivery of an expandable intracorporeal device including an elongate shaft having a proximal section and a distal section. The distal section of the elongate shaft has an elongate belt support member disposed adjacent a portion of the expandable intracorporeal device and a belt which is secured to the belt support member. The belt is circumferentially disposed about the expandable intracorporeal device and has a configuration which constrains the expandable intracorporeal device. A release member releasably secures the belt in the constraining configuration.

Next, the distal end of the delivery system is introduced into the patient's body and advanced to a desired site within the patient's body. The release member is then activated, releasing the belt from the constraining configuration. Optionally, the delivery system may also have an outer protective sheath disposed about the endovascular graft in a constrained state, the belt in its constraining configuration and at least a portion of the release wire disposed at the belt. In such an embodiment, the method of deployment of an expandable intracorporeal device also includes retraction of the outer protective sheath from the endovascular graft prior to activation of the release member.

BRIEF DESCRIPTION OF THE DRAWINGS

FIG. 6A is an enlarged elevational view in partial section of the delivery system in FIG. 1.

FIG. 6B is an enlarged elevational view in partial section of the delivery system of FIG. 1 with portions of the graft and self-expanding members cut away for clarity of view of the belt bushings.

FIG. 12 is an enlarged diagrammatic view of a delivery system having features of the invention disposed within an artery of a patient with an expandable intracorporeal device being deployed within the artery.

FIG. 13 is an elevational view in partial section of a connection between an inflation tube and an inflation port of an endovascular graft.

DETAILED DESCRIPTION

FIGS. 1–8 illustrate an embodiment of delivery system 10 for delivering a variety of expandable intracorporeal devices; specifically, an expandable endovascular graft 11. One such expandable endovascular graft 11 useful for delivery and deployment at a desired site within a patient is disclosed in co-pending U.S. patent application Ser. No. 09/133,978, filed Aug. 14, 1998, by M. Chobotov, which is hereby incorporated by reference in its entirety.

Figure 1:
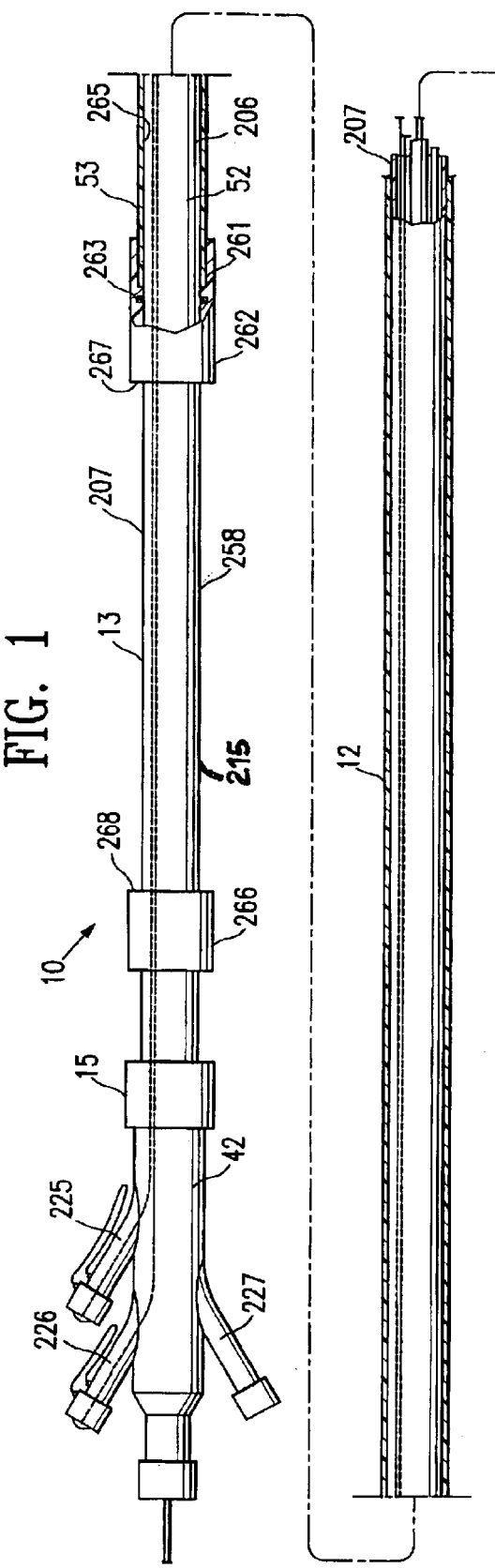
FIG. 1 is an elevational view in partial longitudinal section illustrating an embodiment of a delivery system for an expandable intracorporeal device having features of the invention.
Figure 1:
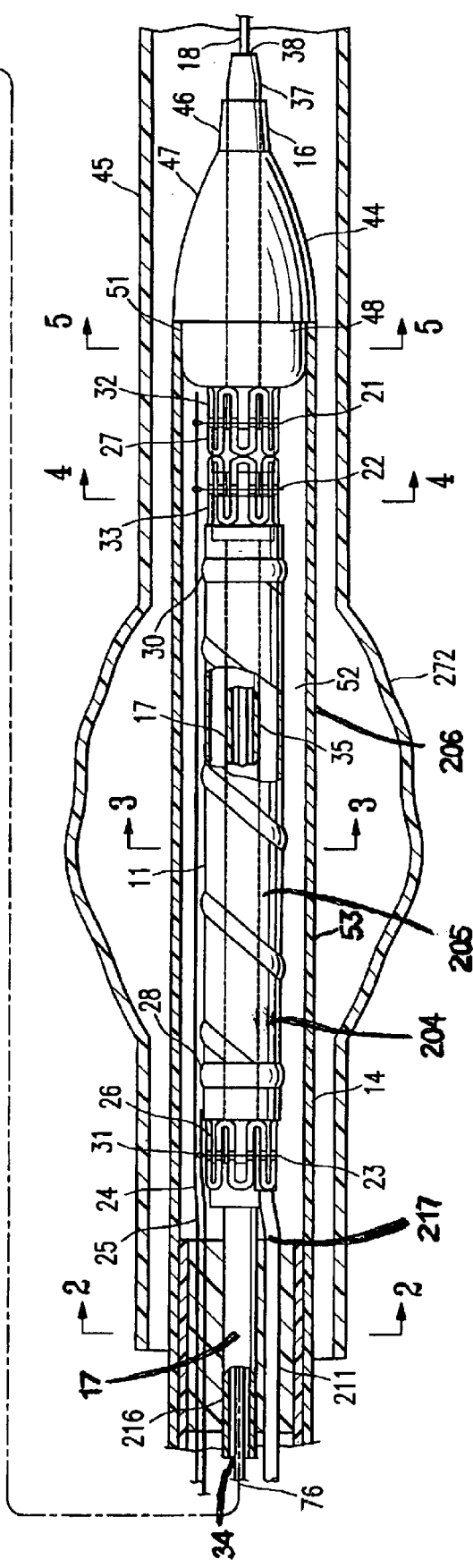

Delivery system 10 in FIG. 1 has an elongate shaft 12 with a proximal section 13, a distal section 14, a proximal end 15 and a distal end 16. The distal section 14 has an elongate belt support member in the form of a guidewire tube 17 disposed adjacent a portion of the expandable intracorporeal device 11. A guidewire 18 is disposed within guidewire tube 17. A plurality of belts 21, 22, and 23 are secured to the guidewire tube 17 and are circumferentially disposed about portions of the endovascular graft 11. FIG. 1 shows the belts in a configuration that constrains the endovascular graft 11. First and second release members 24 and 25 releasably secure belts 21, 22, and 23 in a constraining configuration as shown.

The endovascular graft 11 has a proximal end 26, a distal end 27, a proximal inflatable cuff 28, a distal inflatable cuff 30, a proximal self-expanding member 31, a first distal self-expanding member 32 and a second distal self-expanding member 33. As defined herein, the proximal end of the elongate shaft is the end 15 proximal to an operator of the delivery system 10 during use. The distal end of the elongate shaft is the end 16 that enters and extends into the patient's body. The proximal and distal directions for the delivery system 10 and endovascular graft 11 loaded within the delivery system 10 as used herein are the same. This convention is used throughout the specification for the purposes of clarity, although other conventions are commonly used. For example, another useful convention defines the proximal end of an endovascular graft as that end of the graft that is proximal to the source of blood flow going into the graft. Such a convention is used in the previously discussed co-pending patent application, Ser. No. 09/133,978, although that convention is not adopted herein.

Figure 2:
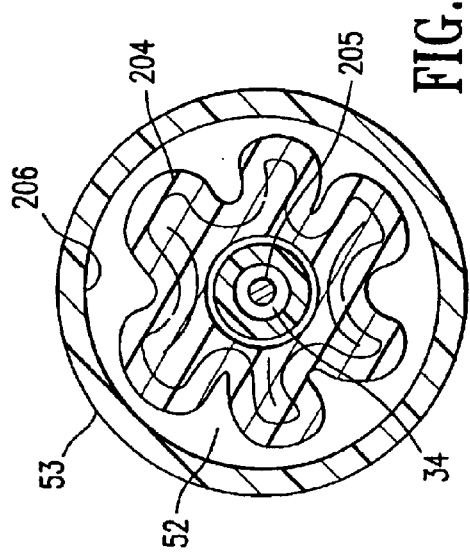
FIG. 2 is a transverse cross sectional view of the delivery system of FIG. 1 taken along lines 2—2 of FIG. 1.
Figure 8:
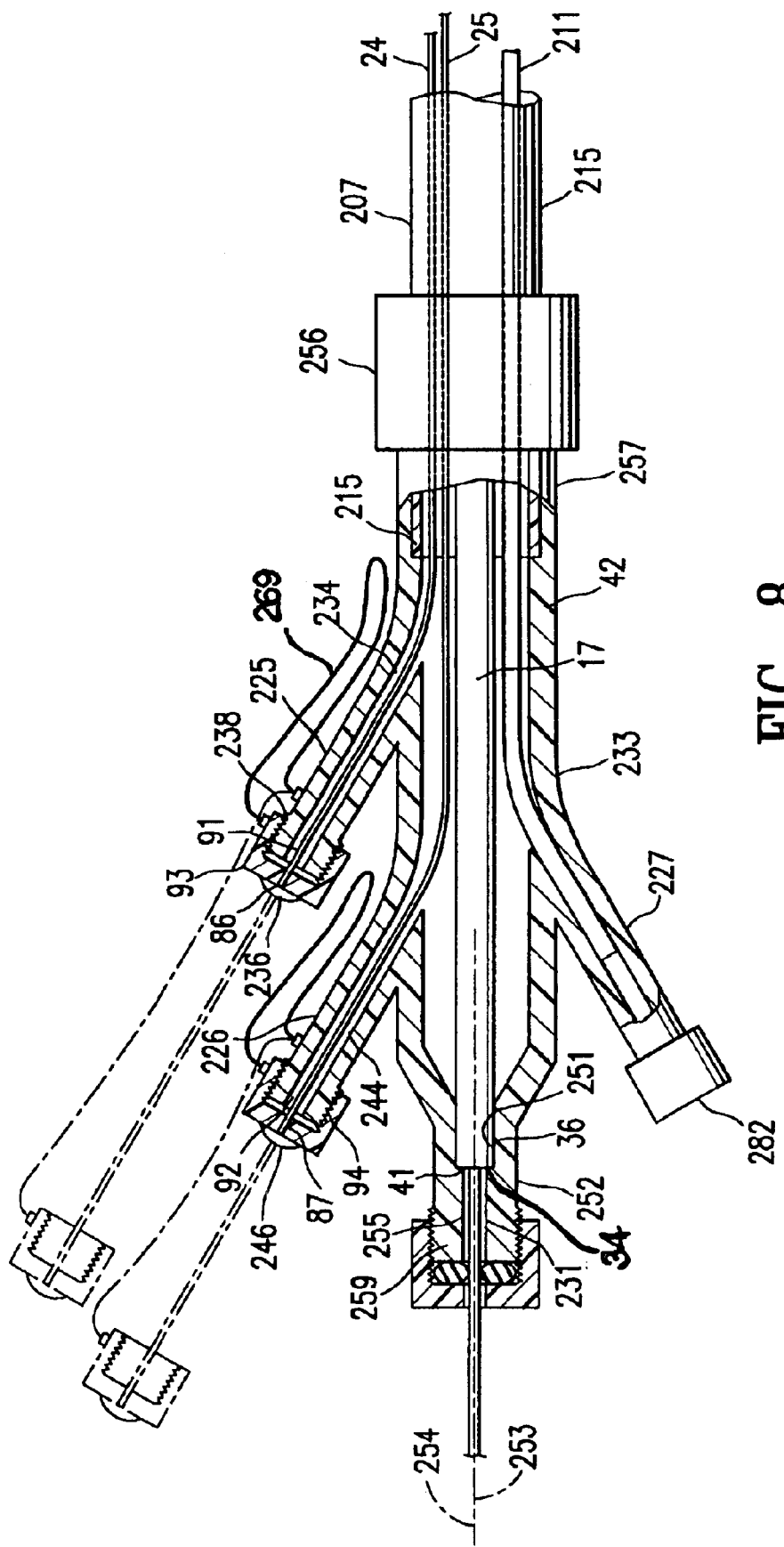
FIG. 8 is an elevational view in partial section of the proximal adapter shown in FIG. 1.
Figure 10:
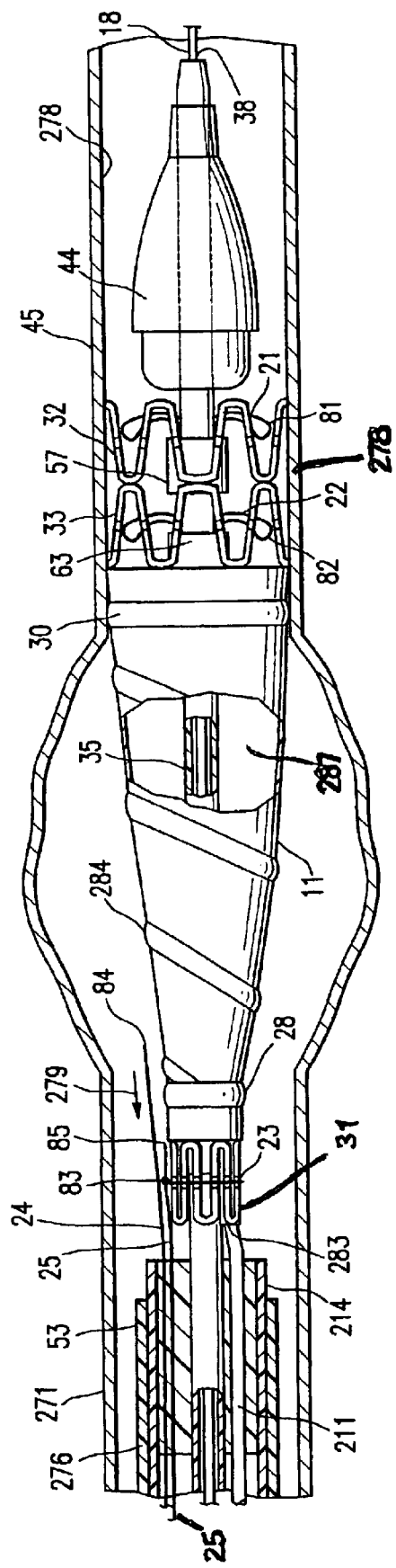
FIG. 10 is a diagrammatic view of a delivery system having features of the invention disposed within an artery of a patient with an expandable intracorporeal device being deployed within the artery.

The guidewire tube 17 has an inner lumen 34, as shown in FIG. 2, a distal section 35, a proximal end 36, as shown in FIG. 8, and a distal end 37. The inner lumen 34 of the guidewire tube 17 terminates at the distal end 37 with a distal guidewire tube port 38, as shown in FIG. 10. As seen in FIG. 8, the proximal end 36 of guidewire tube 17 terminates in a port 41 disposed in the proximal adapter 42. The port 41 is typically a tapered fitting such as a Luer lock fitting which facilitates the attachment of a hemostasis valve (not shown). The guidewire tube 17 is a hollow tubular member that normally has an annular cross section, although oval cross-sectional profiles and others are also suitable.

Figure 5:
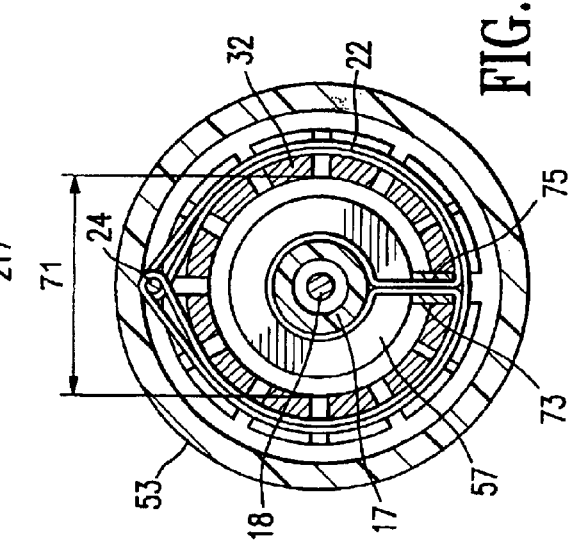
FIG. 5 is a transverse cross sectional view of the delivery system of FIG. 1 taken along lines 5—5 of FIG. 1.

A portion of the distal section 35 of the guidewire tube 17, shown in FIG. 1, is disposed within an inner lumen 43 of a distal nose piece 44, as shown in FIG. 5. Distal nosepiece 44 is configured in a streamlined bullet shape for easy passage within a patient lumen or vessel such as aorta 45. Guidewire tube 17 may be bonded to the inner lumen 43 of the nose piece 44, or it may be molded into the nose piece 44 during manufacture. Referring back to FIG. 1, the nose piece 44 has a distal portion 46, an intermediate portion 47 and a proximal shoulder portion 48 configured to slidingly engage the distal portion 51 of an inner lumen 52 of an outer tubular member 53.

Referring to FIGS. 1, 6A, 6B and 7A, on the distal section 35 of guidewire tube 17, proximal to the proximal shoulder portion 48 of nose piece 44, a first distal belt 21 is secured to the guidewire tube 17. The first distal belt may be secured to the guidewire tube 17 with any suitable adhesive such as cyanoacrylate, epoxy or the like. Both free ends 55 and 56 of the first distal belt 21 are secured to the guidewire tube 17. The guidewire tube 17 may be made from a variety of suitable materials including polyethylene, teflon, polyimide and the like.

Referring to FIGS. 2–5, the inner lumen 34 of the guidewire tube 17 has an inside diameter that can accommodate a guidewire suitable for guiding a device such as delivery system 10. The inner lumen 34 of the guidewire tube 17 may have an inside diameter of about 0.015 inch to about 0.045 inch; specifically, about 0.020 inch to about 0.040 inch. The outer diameter of the guidewire tube 17 may range from about 0.020 inch to about 0.060 inch; specifically, about 0.025 inch to about 0.045 inch.

Referring again to FIGS. 6A, 6B and 7A, an optional first distal belt bushing 57 is disposed about the guidewire tube 17 so as to cover the portions of the free ends 55 and 56 of the first distal belt 21 that are secured to the distal section 35 of the guidewire tube 17. This bushing 57 may also serve to control the constrained configuration of the belted self-expanding members, and may include geometric features to engage or support the belted members. A similar configuration is present at a second distal belt 22 which has free ends secured to the guidewire tube 17 proximal to the first distal belt 21. A second distal belt bushing 63 is disposed about the guidewire tube 17 so as to cover the portions of the free ends of the second distal belt 22 that are secured to the guidewire tube 17. A proximal belt 23 has free ends secured to the guidewire tube 17 proximal to the second distal belt 22 and has an optional proximal belt bushing 67, as shown in FIG. 6, configured similarly to the first and second distal belt bushings 57 and 63.

The belts 21, 22 and 23 can be made from any high strength, resilient material that can accommodate the tensile requirements of the belt members and remain flexible after being set in a constraining configuration. Typically, belts 21, 22 and 23 are made from solid ribbon or wire of a shape memory alloy such as nickel titanium or the like, although other metallic or polymeric materials are possible. Belts 21, 22 and 23 may also be made of braided metal filaments or braided or solid filaments of high strength synthetic fibers such as Dacron®, Spectra or the like. An outside transverse cross section of the belts 21, 22 and 23 may range from about 0.002 to about 0.012 inch, specifically, about 0.004 to about 0.007 inch. The cross sections of belts 21, 22 and 23 may generally take on any shape, including rectangular (in the case of a ribbon), circular, elliptical, square, rectangular, etc.

In general, we have found that a ratio of a cross sectional area of the belts to a cross sectional area of the release members, 24 and 25, of about 1:2 is useful to balance the relative strength and stiffness requirements. Other ratios, however, may also be used depending on the desired performance characteristics.

Figure 4:
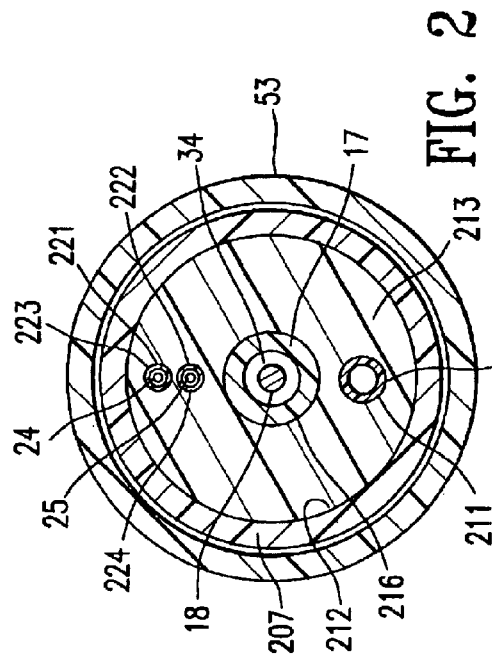
FIG. 4 is a transverse cross sectional view of the delivery system of FIG. 1 taken along lines 4—4 of FIG. 1.

The inner diameters of belt bushings 57, 63 and 67 are sized to have a close fit over the guidewire tube 17 and secured portion 77, as shown in FIG. 7A, of the free ends of the belts 21, 22 and 23 that are secured to the guidewire tube 17. Typically, the inner diameter of the belt bushings 57, 63 and 67 range from about 0.025 inch to about 0.065 inch; specifically, about 0.030 inch to about 0.050 inch. In addition, the outer diameter of belt bushing 57 may be sized to approximate an inner diameter 71, as shown in FIG. 4, of the respective first distal self-expanding member 32 of the endovascular graft 11 when the member 32 is in a fully constrained state. The other belt bushings 63 and 67 may be similarly configured with respect to the second distal self-expanding member 33 and the proximal self-expanding member 31.

Such an arrangement keeps the members 31, 32 and 33 properly situated when in a constrained state and prevents the various portions of the members 31, 32 and 33 from overlapping or otherwise entangling portions thereof while in a constrained state. The outer diameter of the belt bushings 57, 63 and 67 may range from about 0.040 inch to about 0.200 inch; specifically, about 0.060 inch to about 0.090 inch. The material of the belt bushings 57, 63 and 67 may be any suitable polymer, metal, alloy or the like that is bondable. Generally, the belt bushings 57, 63 and 67 are made from a polymer such as polyurethane, silicone rubber or PVC plastic.

As shown in FIG. 7A, belts 21, 22 and 23 extend radially from the guidewire tube 17 through optional standoff tubes 72, 73 and 74. Standoff tubes 72, 73 and 74 are disposed about belts 21–23 adjacent the guidewire tube 17 and act to prevent separation of belts 21–23 in a circumferential direction as tension is applied to the belts. Standoff tubes 72–74 also prevent belts 21–23 from applying other undesirable forces on portions of the endovascular graft 11 that are constrained by the belts. Specifically, the standoff tubes 72–74 prevent the belts 21–23 from spreading the self-expanding members 31–33, or portions thereof, at those locations where the belts 21–23 extend radially through the self-expanding members.

The standoff tubes 72–74 typically have a length substantially equal to a single wall thickness of the self-expanding members 31, 32 and 33. The length of the standoff tubes 72–74 may range from about 0.010 inch to about 0.030 inch. An inner diameter of an inner lumen 75 of the standoff tubes, as shown in FIG. 4, may range from about 0.004 to about 0.024 inch, with a wall thickness of the standoff tubes being about 0.002 inch to about 0.006 inch. Typically, the standoff tubes 72–74 are made from a high strength metal or alloy such as stainless steel, although they may be polymeric as well.

Belts 21–23 exit the outer apertures of standoff tubes 72–74 and extend circumferentially about the respective portions of the expandable intracorporeal device 11. The term "circumferential extension" as used with regard to extension of the belts 21–23 is meant to encompass any extension of a belt in a circumferential direction. The belts may extend circumferentially a full 360 degrees, or any portion thereof. For example, belts or belt segments may extend partially about an endovascular device, and may be combined with other belts or belt segments that also partially extend circumferentially about an endovascular device. Typically, a plane formed by each of the belts 21–23 when in a constraining configuration is generally perpendicular to a longitudinal axis 76, shown in FIG. 1, of the distal section 14 of shaft 12. As shown in FIGS. 6A and 6B, loop ends 81, 82 and 83 of the belts 21, 22 and 23, respectively, are releasably locked together by one or more release members. For example, in the embodiment shown in FIG. 1, a release member in the form of a first release wire 24 is shown disposed within end loops 81 of the first distal belt 21 and end loops 82 of the second distal belt 22 so as to secure the first and second distal belts 21 and 22 in a constraining configuration about the endovascular graft 11. Another release member in the form of a second release wire 25 is shown disposed within end loops 83 of the proximal belt 23 so as to secure the proximal belt 23 in a constraining configuration about the endovascular graft 11.

In some embodiments of the invention, when constrained, the end loops of any single belt touch each other or are spaced closely together such that the belt as a whole forms a substantially circular constraint lying substantially in a plane. Release wire 24 and 25 may be made from suitable high strength materials such as a metal or alloy (e.g., stainless steel) which can accommodate the torque force applied to the release wire by the belt loop ends 83 when the belts 23 are under tension from the outward radial force of the constrained portions of the endovascular graft 11, i.e., the self-expanding member portions 32 and 33.

The release wires 24 and 25 may generally have an outer diameter ranging from about 0.006 to about 0.014 inch. Distal end portions 84 and 85 of release wires 24 and 25, respectively, may terminate at any appropriate site distal of the loop ends 81–83 of belts 21–23. As shown in FIG. 8, the proximal ends 86 and 87 of the release wires 24 and 25 extend through the elongate shaft 12 of the delivery system 10 through proximal ports 91 and 92 on the proximal adapter 42, respectively, and terminate at respective release wire handles 93 and 94 which are releasably secured to the proximal adapter 42.

FIG. 7B illustrates an alternative embodiment of the belts 21–23 of FIG. 7A. In FIG. 7A, belts 21–23 are shown as each consisting of a single strand of wire formed into two loop ends, 81–83, respectively, with the loop ends overlapping each other. Free ends 55 and 56 of belt 81 are shown secured to the distal section of the guidewire tube 35. In contrast, FIG. 7B, wherein like elements with regard to FIG. 7A are shown with like reference numerals, shows belts 21B–23B formed of two strands of wire, with each strand formed into a single loop which overlaps a loop of the other strand to form loop ends 81B–83B. The free ends of the belts 21B–23B may be secured in a similar manner to those of free ends 55 and 56 of FIG. 7A.

Turning now to FIGS. 7C and 7D, alternative embodiments for portions of the delivery system of the present invention are shown. FIGS. 7C and 7D illustrate alternative belts 21C, 22C and 23C disposed on guidewire tube 17. Single or multiple belts 21C–23C may be deployed at various locations along guidewire tube 17 as desired. In addition, the members comprising belts 21C–23C are shown as a single line. However, belts 21C–23C may be of a single- or multiple strand or filament design with various cross-sectional shapes as previously described. A single solid ribbon or wire is particularly useful.

Belts 21C–23C shown in FIGS. 7C and 7D are a single strand filament wrapped around guidewire tube 17 and fixed thereon via any number of suitable techniques, such as gluing with adhesive, mechanical fixation, etc. Especially useful is fixing the belt with an ultraviolet-curable adhesive.

Belt 21C includes belt arms 112 and 114, each of which, in the embodiments shown, is a loop of filament twisted upon itself to form a helix. Any number of twists may be imparted to arms 112 and 114 to provide a relatively loose or relatively tight helix as desired. Typically the number of twists (with a single twist being defined as a single overlap of wire segment) in each belt arm 112 and 114 numbers from zero to about 50 or more; specifically, about two to about 10. The choice of material used for belt 21C is an important factor in determining the optimum number of twists for each belt arm. Belt arms 112 and 114 may be formed into other configurations (e.g., braid, double helix, etc.) as well.

Disposed within the distal ends or loops 116, 118 of the belt arms 112 and 114 are distal apertures or openings 120, 122, respectively. During assembly of the delivery system, a release wire (such as wire 24) is passed through each aperture 120, 122 after the belt arms are wrapped around the graft self-expanding member, preferably in a circumferential groove as further described below. The release wire may also be disposed through any aperture created along the length of belt arms 112, 114 by each helix twist, although the distal-most apertures 120, 122 are preferred.

The wire optionally may be welded, glued, or otherwise fixed to itself at discrete points or along all or any portion of belt arms 112, 114, save distal ends 116 and 118 and their corresponding apertures 120 and 122. For instance, the belt arm wire may be glued or welded to itself at the overlap or twist points, such as points 124.

FIG. 7D shows an optional belt arm sleeve 126 that may be used to enclose a portion of one or both belt arms 112, 114, or any of the other belt embodiments contemplated herein. Belt 112 is shown in FIG. 7D being constrained or covered over a length thereof by a flexible sleeve or coating 126 (or alternatively, a coil wrapping or by fixing the loop to itself by adhesives, welding, soldering, brazing, etc.). Sleeve or coating 126 may optionally be shrink-wrapped, crimped, or otherwise configured to constrain or cover belt 112 therein. These fixation and sleeve features help to minimize the potential of belt arm untwisting and tend to close or block some or all of the helix apertures along the length except those through which the release wire are intended to pass. They can also provide greater structural and operational stability to the catheter system as a whole.

Belt arm sleeve 126 can be configured to have a transverse dimension that is sized to fit a twisted belt arm with fixed nodal points such as the belt arm 112 shown in FIG. 7D. In order to accommodate such a twisted belt arm 112, the inner diameter and outer diameter would be large relative to a transverse dimension of the wire material that forms the belt arm 112. However, the belt arm sleeve 126 can also be only slightly larger in transverse dimension that the wire that forms the belt arm. For example, embodiments of belt arms that do not have twisted wires may have a sleeve 126 that fits closely or tightly over two strands of wire forming a belt arm. The sleeve 126 can cover substantially the entire length of such an untwisted belt arm from at least the guidewire tube to just proximal of the distal loop, such as distal loop 120. The distal loop should remain exposed for engagement by a release wire. In such an embodiment, the sleeve covered portion of the belt arm may also be wrapped around an secured to the guidewire tube just as the unsleeved belt portion of the belt arm 112 shown in FIG. 7D is shown at 71C. This type of low profile belt arm sleeve may also be used to cover twisted belt arm embodiments, although a slightly larger diameter sleeve would be required.

It may be desirable to impart a particular free resting angle to the belt arms 112, 114 to improve the reliability of the system and further reduce the possibility of the arms 112 and 114 interfering with other components of the prosthesis or delivery system. The FIG. 7C view shows belt arms 112, 114 symmetrically disposed at an angle α as measured from a horizontal plane 125. This angle α may range from zero to 180 degrees. For example, one or both belt arm 112, 114 may lie along plane 125 or they may rest in the configuration shown (α=45 degrees). Any known techniques may be used to impart a desired resting configuration to the system, such as, for example, cold working or shape-setting by way of an a thermal phase transformation (in the case of shape memory alloys).

This helix configuration shown in the embodiment of FIGS. 7C and 7D is a particularly reliable configuration. It reduces the possibility that a portion of belt 81C becomes entangled with a self-expanding member (such as members 31, 32 and 33) or otherwise interferes with the safe and effective deployment of the prosthesis.

FIG. 7E depicts a particularly useful arrangement for configuring the belt end loops 81–83 with release wires 24–25 during assembly of delivery system 10. In this example, first and second end loops 81' and 81" of belt 21 are shown connected via release wire 24. To achieve the configuration of FIG. 7E, first end loop 81' is passed through aperture 88 disposed in second end loop 81". A portion of aperture 89 disposed in first end loop 81' should extend through the plane created by second end loop 81" as shown in FIG. 7E.

Next, release wire 24 is passed through the portion of aperture 89 that extends beyond this plane so that wire 24 "locks" the two looped ends 81' and 81" together as shown. We have found that this is a stable configuration that lends itself well to a reliable and safe deployment protocol.

Other techniques for assembling wire 24 and end loops 81' and 81" may be used; the method described above is merely exemplary. Wire 24 may simply pass through loop ends as configured and as shown at reference numerals 81, 82 and 83 in FIG. 7A, and 81B, 82B and 83B of FIG. 7B as well.

In the embodiment of FIG. 7F, an even more general and simple alternative arrangement for belt 81 is taught. Here, belt 110 is a member in the shape of a wire in which its distal end forms loop 116 having an aperture 120 for receiving a release wire. This arrangement may be used on one or both ends of belt 110 or, alone if belt 110 is in the form of a single belt arm as discussed above. Connection 123 is shown in FIG. 7F as a simple wrapping of the distal end of the wire comprising belt distal end loop 116. Connection 123 need not be limited to such a tapered or cylindrical sleeve or coating, however. Other methods to form distal end loop 116 are contemplated, including, for example, the use of adhesives, welding, brazing, soldering, crimping, etc. An optional protective sleeve or coating 127 (shown in sectional view in FIG. 7F) covers or is part of connection 123 and serves to protect the patient as well as components of the delivery system and prosthesis from damage.

Turning now to FIGS. 7G and 7H, two alternative embodiments of a ribbon-like belt 21G and 21H are shown. In FIG. 7H, a section 128 of material has been partially displaced from belt 21G distal end 116 and worked into a loop-like member 129 such that two generally orthogonal apertures 130, 132 are formed in belt distal end 116. A set of hinges or other protective mechanism or material may be used on each end of this member 128 so that further tearing or peeling of this member may be prevented. Section 128 may be formed integrally from the belt distal end as shown in FIG. 7G or may be a separate component that is attached to the belt distal end by any suitable means.

Second belt distal end 118 in FIG. 7G is shown as having an aperture 133 disposed therein. In use, a half-twist is imparted to the ribbon-like belt as the second distal end 118 is brought through aperture 130 such that apertures 132 and 133 are at least partially aligned. A release wire (such as wire 24) is then brought through apertures 132 and 133 to releasably join ends 116 and 118.

FIG. 7H shows yet another embodiment of a belt 81H where a simple rectangular aperture 132 is disposed in the distal end 116 of belt281H through which another belt end and release wire may be disposed as taught herein. As with the embodiment of FIG. 7G, a half-twist is imparted to the belt 21H in use so that the second distal end 118 is brought through aperture 132. A release wire may then be threaded through apertures 132 and 133 to releasably join ends 116 and 118. In this embodiment, aperture 132 should be large enough to accommodate both second distal end 118 and a release wire.

Figure 7I:
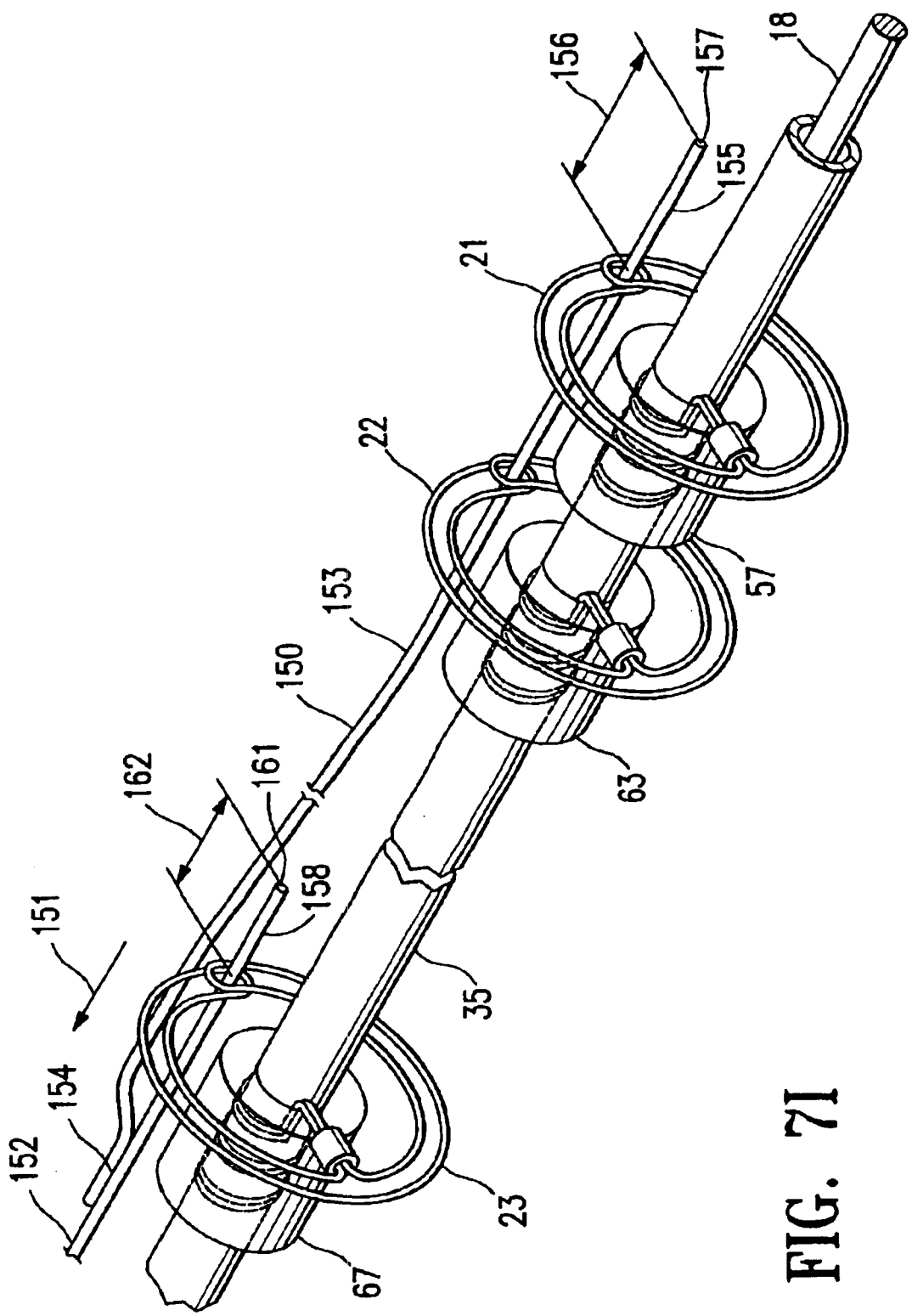
FIG. 7I is a perspective view of an alternative embodiment of a branched release wire.
Figure 7K:
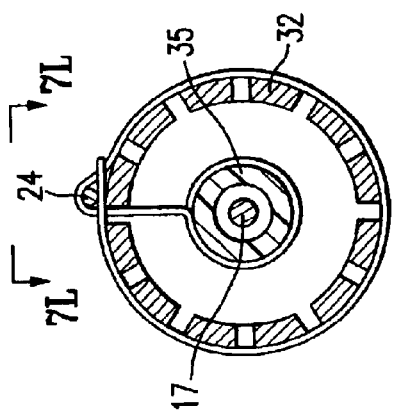
FIG. 7A is a perspective view showing release belt configurations having features of the invention.
FIG. 7B is a perspective view showing an alternative embodiment of release belts.
FIG. 7C is an end view showing an alternative embodiment of release belts.
FIG. 7D is a perspective view of the embodiment of FIG. 7C.
FIG. 7E is an enlarged view of a particular coupling configuration between end loops of release belts.
FIG. 7F is a perspective view, partially cut away, of a particular embodiment of an end loop of a release belt.
FIG. 7G is a perspective view of an alternative embodiment of a release belt.
FIG. 7H is a perspective view of an alternative embodiment of a release belt.
Figure 7L:
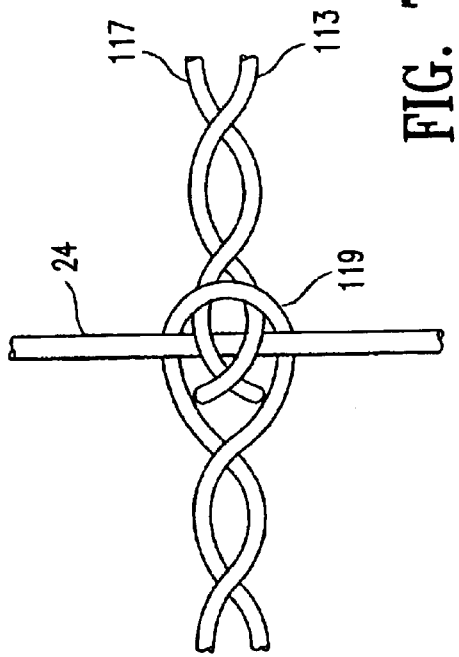
Figure 7J:
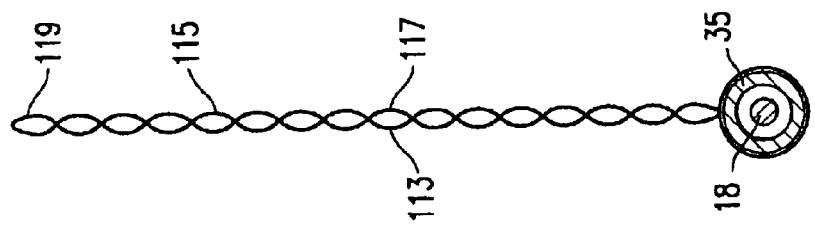

FIG. 7I shows a perspective view of a belt assembly similar to that shown in FIG. 7A, wherein like elements are shown with like reference numerals. An alternative embodiment of a release wire consisting of a branched release wire 150 is illustrated. The branched release wire engages the belts 21–23 and is configured to release belts 21–23 at different times with a continuous proximal withdrawal movement, the direction of which is indicated by arrow 151, of the branched release wire 150. Branched release wire has a main portion 152 and a branch portion 153. Branch portion 153 is secured to main portion 152 by a solder joint 154. The joint 154 could also be made by any other suitable means, such as welding, bonding with an epoxy, mechanically binding the joint, or the like. Branch portion 153 engages first distal belt 21 and second distal belt 22. A distal segment 155 has a length L indicated by arrow 156 which extends distally from first distal belt 21 to the distal end 157 of branch portion 153.

Main portion 152 of the branched release wire 150 engages the proximal belt 23 and has a distal segment 158 that extends distally from the proximal belt 23 to a distal end 161 of the main portion. The length L' of the distal segment 158 of the main portion 152 is indicated by arrow 162. Length L of distal segment 155 is greater than length L' of distal segment 158. In this way, as the branched release wire is withdrawn proximally, proximal belt 23 is released first, first distal belt 21 is released second and second distal belt 22 is released last. Such a branched release wire allows a wide variety of belt release timing with a single continuous withdrawal or movement of a proximal end (not shown) of the branched release wire 150. The proximal end of the branched release wire may be terminated and secured to a release wire handle or the like, as discussed herein with regard to other embodiments of release wires. The ability to deploy multiple release wires in a desired timing sequence with a single branched release wire 150 gives the designer of the delivery system great flexibility and control over the deployment sequence while making the deployment of the belts simple and reliable for the operator of the delivery system. Although the branched release wire 150 has been shown with only a single branch, any number of branches or desired configuration could be used to achieve the deployment sequence required for a given embodiment of a delivery system. For example, a separate branch could be used for each belt in a multiple belt system, with varying distal segment length used to control the sequence of deployment. Also, multiple branched release wires, or the like, could be used in a single delivery system to achieve the desired results.

A number of embodiments for the belt and belt arm components of the present invention are described herein. In general, however, we contemplate any belt or belt arm configuration in which the belt may be used to releasably hold or restrain a implant member in conjunction with a release member. The particular embodiments disclosed herein are not meant to be limiting, and other variations not explicitly disclosed herein, such as those in which multiple apertures (which may have varying shapes and sizes) are disposed along the belt length, those in which the belt or belt arm distal ends comprises a separate material or element that is affixed to the belt or belt arm, etc. are within the scope of the invention. Furthermore, various embodiments of the ends of the belts or belt arms taught herein may exist in any combination in a single delivery system.

Turning now to FIG. 6A, belts 21–23 lie within circumferential grooves or channels 95, 96 and 97, respectively, formed into the respective self-expanding members 31, 32 and 33. Grooves 95–97 prevent axial displacement of the belts 21–23 prior to activation or release of the releasable members 24 and 25, i.e., proximal retraction of the first and second release wires. Although grooves 95–97 are illustrated in the embodiment shown, other alternatives are possible to achieve the same or similar function of the grooves. For example, abutments extending slightly from the self-expanding members 31–33 on either side of the belts 21–23 in their constraining configuration could prevent axial movement of the belts. A detachable adhesive or the like could also be used.

As shown in FIG. 10, the release of looped ends 81–83 occurs when the distal end portions 84 and 85 of the release wires 24 and 25, respectively, pass from within the overlapped looped ends 81–83. If the looped ends 81–83 move axially in response to movement of the release wires 24 and 25 due to frictional forces imposed on the looped ends by the release wires, the point at which the distal ends of the release wires 84 and 85 pass from within the looped ends 81–83 would vary depending on the amount of movement of the looped ends 81–83.

If the looped ends 81–83 were to be axially displaced from their normal position relative to the distal ends of the release wires prior to deployment, the timing of the release of the belts 21–23 could be adversely affected. Thus, the prevention of axial displacement of the belts 21–23 during proximal retraction of the release wires 24 and 25 facilitates accurate release of the belts by keeping the overlap joint of the belt looped end portions in a constant axial position during such retraction.

In addition, it may be desirable to keep belts 21–23 positioned at or near the general center of a given constrained self-expanding members 31–33 so that the self-expanding member 31–33 is substantially uniformly and evenly constrained over its axial length. If belts 21–23 constrain the self-expanding members 31–33 at a non-centered axial position on the member, an end of the member opposite that of the non-centered position may be less constrained and may interfere with axial movement of the outer tubular member 53 (and consequently deployment of the endovascular graft 11).

Figure 3:
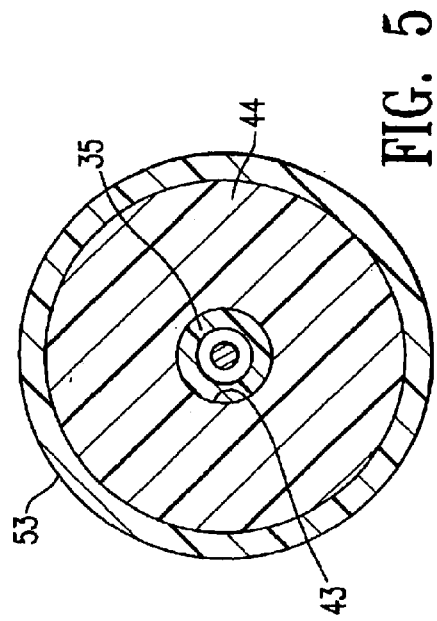
FIG. 3 is a transverse cross sectional view of the delivery system of FIG. 1 taken along lines 3—3 of FIG. 1.

Tubular body member 205 of the endovascular graft 11 is disposed between and secured to the second distal self-expanding member 33 and the proximal self-expanding member 31. The tubular body member comprised of flexible material 204, is shown constrained in an idealized view in FIGS. 1, 3 and 6A, for clarity. In practice, tubular body member 205 while constrained is tightly compressed with minimal air space between layers of flexible material 204 so as to form a tightly packed configuration as shown in FIG. 3. Tubular body member 205 is optionally radially constrained by an inside surface 206 of the inner lumen 52 of outer tubular member 53.

An inner tubular member 207 is slidably disposed within the inner lumen 52 of outer tubular member 53. Release wires 24 and 25, guidewire tube 17 and an inflation tube 211 are disposed within an inner lumen 212 of the inner tubular member 207. Inner lumen 212 is optionally sealed with a sealing compound, depicted in FIGS. 1, 2 and 6A by reference numeral 213 at distal end 214. The sealing compound 213 prevents leakage of fluids such as blood, etc., from a proximal end 215, shown in FIG. 8, of the inner tubular member 207. As shown in FIG. 2, sealing compound 213 fills the space within the inner lumen 212 of the inner tubular member 207 between an outer surface 216 of the guidewire tube 17, the outer surface 217 of the inflation tube 211 and the outer surfaces 221 and 222 of the tubular guide 223 for the first release wire 24 and the tubular guide 224 for the second release wire 25. The sealing compound 213 can be any suitable material, including epoxies, silicone sealer, ultraviolet cured polymers, or the like.

In FIG. 2, the tubular guides 223 and 224 for the first release wire 24 and the second release wire 25 allow axial movement of the release wires with respect to the sealing compound 21 3 and inner tubular member 207. The inside diameter of the inner lumens of the tubular guides 223 and 224 are sized to fit closely with an outer diameter or transverse dimension of the release wires 24 and 25. Alternatively, tubular guides 223 and 224 may be replaced by a single tubular guide that houses one or more release wires, such as wires 24 and 25.

Turning to FIG. 8, the inner tubular member 207 terminates proximally with the proximal adapter 42 having a plurality of side arms 225, 226 and 227 and a proximal exit port 231 for the inner lumen 34 of the guidewire tube 17. First release wire side arm 225 branches from the proximal adapter body portion 233 and has an inner lumen 234 and proximal end 86 of the first release wire 24. A proximal extremity 236 of the first release wire 24 is anchored to the first release wire proximal handle 93 which is threaded onto the proximal end 238 of the first release wire side arm 225. The proximal extremity 236 of first release wire 24 is configured as an expanded bushing or other abutment that captures the handle 93 and translates proximal axial movement of the handle 93 to the first release wire 24 but allows relative rotational movement between the handle 93 and the proximal end 86 of the first release wire 24.

A similar configuration exists for the proximal end 87 of the second release wire 25. There, a second release wire side arm 226 branches from the proximal adapter body 233 and has an inner lumen 244 that houses the proximal end 87 of the second release wire 25 which is free to slide in an axial orientation within the lumen 244. A proximal extremity 246 of the second release wire 25 is configured as an expanded bushing or other abutment that captures the second release wire handle and translates axial proximal movement of the second release wire handle 94 to the second release wire 25, but allows relative rotational movement between the proximal end 87 of the second release wire 25 and the second release wire handle 94.

The first release wire handle 93 and second release wire handle 94 may optionally be color coded by making each, or at least two, release wire handles a color that is distinctly different from the other. For example, the first release wire handle 93 could be made green in color with the second release wire handle 94 being red in color. This configuration allows the operator to quickly distinguish between the two release wire handles and facilitates deployment of the belts in the desired order.

In another embodiment, instead of color coding of the release wire handles 93 and 94, the spatial location of the handles can be configured to convey the proper order of deployment of the release wires to the operator of the delivery system. For example, if three release wire handles are required for a particular embodiment, the corresponding three side arms can be positioned along one side of the proximal adapter. In this configuration, the release wire handle that needs to be deployed first can extend from the distal-most side arm. The release wire handle that needs to be deployed second can extend from the middle side arm. The release wire handle that is to be deployed last can extend from the proximal-most side arm. For such a configuration, the operator is merely instructed to start deployment of the release wires at the distal-most release wire handle and work backward in a proximal direction to each adjacent release wire handle until all are deployed. Of course, an opposite or any other suitable configuration could be adopted. The configuration should adopt some type of spatially linear deployment order, either from distal to proximal or proximal to distal, in order to make reliable deployment of the release wires in the proper order easy to understand and repeat for the operator of the delivery system. Other types of release order indicators such as those discussed above could also be used, such as numbering each release wire handle or side arm with a number that indicates the order in which that handle is to be deployed.

As shown in FIG. 8, the proximal end 36 of the guidewire tube 17 terminates and is secured to an inner lumen 251 of the proximal end 259 of the proximal adapter 42. Inner lumen 251 typically has a longitudinal axis 253 that is aligned with a longitudinal axis 254 of the proximal section of elongate shaft 12 so as to allow a guidewire to exit the proximal end 15 of the elongate shaft 12 without undergoing bending which could create frictional resistance to axial movement of the guidewire. A proximal port 255 of the proximal adapter 42 may be directly fitted with a hemostasis valve, or it may be fitted with a Luer lock fitting which can accept a hemostasis valve or the like (not shown).

The proximal adapter 42 may be secured to the proximal end 215 of the inner tubular member 207 by adhesive bonding or other suitable method. A strain relief member 256 is secured to the distal end 257 of the proximal adapter 42 and the inner tubular member 207 to prevent kinking or distortion of the inner tubular member 207 at the joint.

As seen in FIG. 1, the proximal end 261 of the outer tubular member 53 is secured to a proximal fitting 262 that slides over an outer surface 258 of the inner tubular 207 member. A seal 263 located in proximal fitting 262 provides a fluid seal for the lumen 265 formed between the outer surface 258 of the inner tubular 207 member and the inner surface 206 of the inner lumen 52 of the outer tubular member 53. The fit between the outer surface 258 of the inner tubular member 207 and the inner surface 206 of the outer tubular member 53 is typically close, but still allows for easy relative axial movement between outer tubular member 53 and inner tubular member 207. A stop 266 is disposed and secured to the outer surface 258 of the inner tubular member 207 distal of the proximal adapter 42 to limit the amount of proximal axial movement of the outer tubular member 53 relative to the inner tubular member 207.

When the outer tubular member 53 is positioned on the proximal shoulder 48 of the distal nose piece 44 prior to deployment of endovascular graft 11, the distance between a proximal extremity 267 of proximal fitting 262 and a distal extremity 268 of stop 266 is approximately equal to or slightly greater than an axial length of the endovascular graft 11 in a constrained state. This configuration allows the outer tubular member 53 to be proximally retracted to fully expose the endovascular graft 11 in a constrained state prior to deployment of the graft. This distance may be greater, but should not be less than the length of the endovascular graft 11 in a constrained state in order to completely free the constrained graft 11 for radial expansion and deployment.

Retraction limiters may alternatively be used to prevent excessive axial movement of the release wires 24 and 25 in a proximal direction during deployment. Particularly in embodiments of the invention where single release wires are used to constrain and deploy multiple belts such as with first release wire 24, retraction limiters may be used to allow enough axial movement of the release wire 24 to deploy a first belt 21, but prevent deployment of a second more proximally located belt 22. For example, as shown in FIG. 8, a retraction limiter in the form of a filament 269 could be disposed between the proximal adapter 42 and the handle 93 of the first release wire 24 such that proximal retraction of the first release wire 24 sufficient for deployment of the first distal belt 21 could be achieved, but not so much as to allow deployment of the second distal belt 22. In order to deploy the second distal belt 22, the filament 168 would have to be severed or otherwise released. This type of configuration can allow more control over deployment of the endovascular graft 11 and allow deployment in stages which are sequentially controlled to prevent inadvertent deployment of a portion of the graft 11 in an undesirable location within the patient's vessels.

Figure 9:
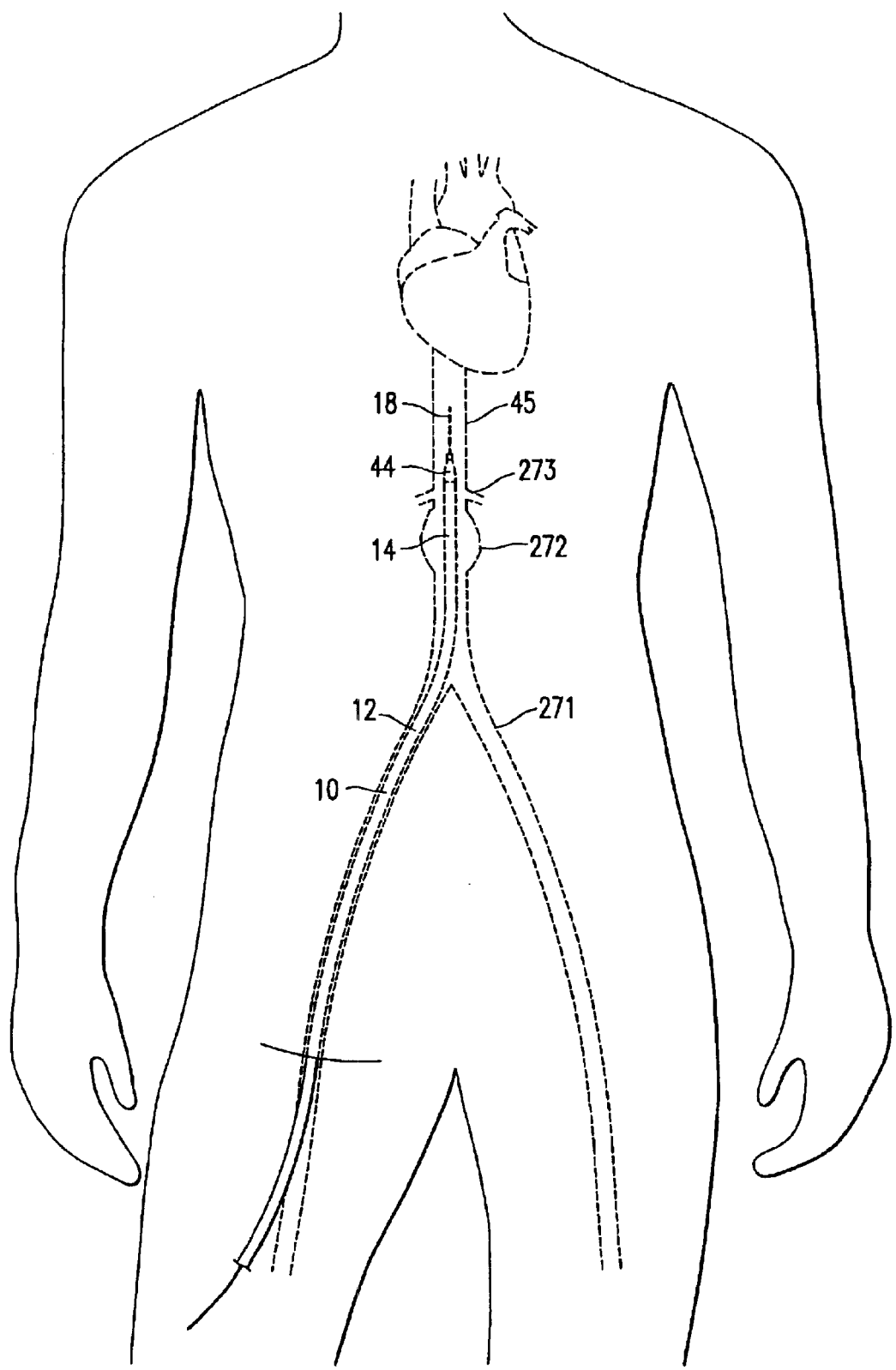
FIG. 9 is a diagrammatic view of a patient's body illustrating the patient's heart, aorta, iliac arteries, femoral arteries, and a delivery system having features of the invention disposed within the femoral artery and aorta.

In use, the delivery system 10 is advanced into a patient's arterial system 271 percutaneously as shown in FIG. 9 and positioned so that the endovascular graft 11 spans an aneurysm 272 in the patient's aorta 45 as illustrated in FIGS. 1 and 9–12. It is generally desirable to have the tubular body portion 205 of the graft 11 positioned below the renal arteries 273 in order to prevent significant occlusion of the renal arteries. The procedure typically begins with the placement of guidewire 18 into the patient's target vessel across the target location, e.g., the aneurysm 272. Common percutaneous techniques known in the art may be used for the initial placement of the guidewire 18. For example, as shown in FIG. 9, percutaneous access to the aorta may be had through the femoral or iliac artery, although other access sites may be used. The delivery system 10 may then be advanced over the guidewire 18 to a desired position within the patient's vessel 45. Alternatively, delivery system 10 and guidewire 18 could be advanced together into the patient's vasculature 271 with the guidewire 18 extending distally from the distal port 38 of the guidewire tube 17. In addition, it may be desirable in some cases to advance the delivery system 10 to a desired location within the patient without the use of a guidewire 18.

Figure 11:
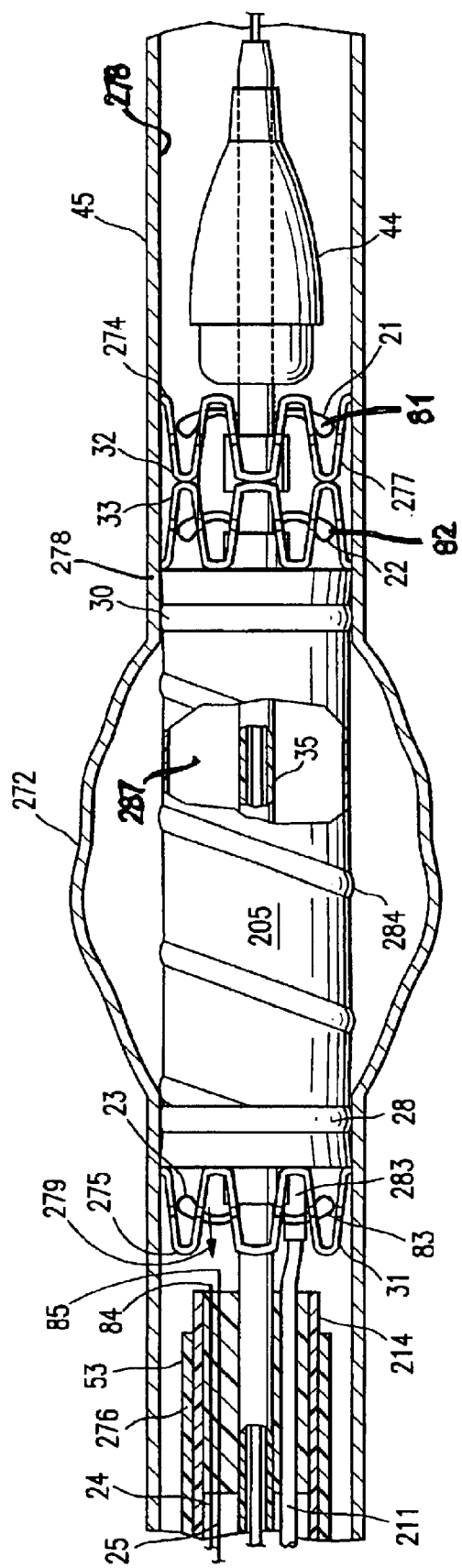
FIG. 11 is a diagrammatic view of a delivery system having features of the invention disposed within an artery of a patient with an expandable intracorporeal device being deployed within the artery.

Generally, the position of the delivery system 10 is determined using fluoroscopic imaging or the like. As such, it may be desirable to have one or more radiopaque markers (not shown) secured to the delivery system at various locations. For example, markers may be placed longitudinally coextensive with the respective distal and proximal extremities 274 and 275, as shown in FIG. 11. In this way, it can be readily determined whether the graft 11 is spanning the aneurysm 272 of the patient's artery. Imaging markers, such as radiopaque markers, may also be secured to desirable positions on the endovascular graft 11 itself. Other types of imaging and marking systems may be used such as CT, MRI and NMR imaging systems and markers.

Once the distal section 14 of 12 of the delivery system 10 is properly positioned within the patient's artery 45, the operator moves the proximal end 261 of outer tubular member 53 in a proximal direction relative to inner tubular member 207. The relative axial movement is carried out by grasping the proximal end 215 of the inner tubular member 207 or proximal adapter 42, and grasping the proximal end 261 of the outer tubular member 53, and moving the respective proximal ends towards each other. This retracts the distal section 276 of the outer tubular member 53 from the constrained endovascular graft 11 and frees the graft for outward radial expansion and deployment. However, in this deployment scheme, note that the operator is free to reinsert graft 11 back into the outer tubular member 53 if necessary, as the release bands have not yet released the graft.

Once the distal section 276 of the outer tubular member 53 has been retracted, handle 93 of the first release wire 24 may then be unscrewed or otherwise freed from the proximal adapter 42 and retracted in a proximal direction indicated by arrow 279 in FIG. 10 until the distal end 84 of the first release wire 24 passes from within the looped ends 81 of the first distal belt 21. When this occurs, the looped ends 81 of the first distal belt 21 are released and the first distal belt 21 ceases to radially constrain the first distal self-expanding member 32 and that member 32 self-expands in a radial direction into an inner surface 278 of the patient's aorta 45 as shown in FIG. 10.

If the operator of the delivery system 10 is not satisfied with the position, particularly the axial position, of the endovascular graft 11 after deployment of the first distal self-expanding member 32, it may then be possible to re-position the endovascular graft 11 by manipulating the proximal end 15 of the elongate shaft 12. Movement of the elongate shaft 12 can move the endovascular graft 11, even though physical contact between the expanded member 32 and the vessel inner surface 278 generates some static frictional forces that resist such movement. It has been found that the endovascular graft 11 can be safely moved within a blood vessel 45 even in the state of partial deployment discussed above, if necessary.

Once the operator is satisfied with the position of the graft 11, the first release wire 24 may then be further proximally retracted so as to deploy the second distal belt 22 in a manner similar to the deployment of the first distal belt 21. The deployment of the second distal belt 22 occurs when the distal end 84 of the first release wire 24 passes from within looped ends 82 of the second distal belt 22 which are held in a radially constraining configuration by the first release wire 24. Upon release of the second distal belt 22, the second distal self-expanding member 33 expands in a radial direction such that it may engage inner surface 278 of the patient's aorta 45. The amount of outward radial force exerted by the self-expanding members 32 and 33 on the inside surface 278 of the patient's aorta 45, which may vary between members 32 and 33, is dependent upon a number of parameters such as the thickness of the material which comprises the self-expanding members 32 and 33, the nominal diameter which the self-expanding members 32 and 33 would assume in a free unconstrained state with no inward radial force applied, material properties of the members and other factors as well.

Once the distal members 32 and 33 are deployed, the handle 94 for the second release wire 25 can be disengaged and axially retracted in a proximal direction from the proximal adapter 42 until the distal end 85 of the second release wire 25 passes from within the looped ends 83 of the proximal belt 23. Once the proximal belt 23 is released, the proximal self-expanding member 31 is deployed and expands in an outward radial direction, such that it may engage or be in apposition with the inner surface 278 of the patient's aorta 45 as shown in FIG. 11. Thereafter, the endovascular graft 11 may be inflated with an inflation material (not shown) injected into the proximal injection port 282 in the proximal adapter 42, through the inflation tube 211, and into the inflation port 283 of the endovascular graft 11. Inflation material may be injected into the inflation port 283 until the proximal and distal inflatable cuffs 28 and 30 and inflatable channels 284 of the graft 11 have been filled to a sufficient level to meet sealing and other structural requirements necessary for the tubular body to meet clinical performance criteria.

Once graft 11 is fully deployed, a restraining or retention device, such as retention wire 285 that binds the distal end 286 of the inflation tube 211 to the inflation port 283, as shown in FIGS. 12 and 13, is activated. The retention wire 285 is activated by pulling the proximal end of the wire in a proximal direction so as to disengage the distal ends 293 and 294 from the holes 295 and 296. This eliminates the shear pin function of the distal ends 293 and 294 and allows the distal end 286 of the inflation tube 211 to be disengaged from the inflation port 283. The release wires 24 and 25 may then be fully retracted from the elongate shaft 12 in a proximal direction and the delivery system 12 retracted in a proximal direction from the deployed endovascular graft 11. The unconstrained distal belts 21–23 slip through the openings in the expanded members 31, 32 and 33 as the delivery system 12 is retracted and are withdrawn through the inner passageway 287 of the deployed graft 11. The distal nosepiece 44 is also withdrawn through the inner passageway 287 of the deployed graft 11 as the delivery system 12 is withdrawn as shown in FIGS. 10–12.

FIG. 13 illustrates the junction between the distal end 286 of inflation tube 211 and inflation port 283. Typically, retention wire 285 extends from the inflation port 283 proximally to the proximal end 15 of delivery system 10. In this way, an operator can disengage the distal end 286 of the inflation tube 211 from the inflation port 283 by pulling on the proximal end 283 of retention wire 285 from a proximal end 15 of delivery system 10. The retention wire 285 can be a small diameter wire made from a material such as a polymer, stainless steel, nickel titanium, or other alloy or metal; in a particular embodiment of the invention, retention wire 285 may be a spring formed of a variety of suitable spring materials. Alternatively retention wire 285 may have a braided or stranded configuration.

FIG. 13 shows a single retention filament or wire 285 is disposed within the lumen 291 of the inflation tube 211. The distal end 292 of retention wire 285 may have one or more loops 293 and 294, respectively, disposed within one or more side holes disposed in the inflation port 283 of the distal end 286 of the inflation tube 211. A number of side hole configurations may be utilized. The embodiment of FIG. 13 has two sets of opposed side hole locations 295 and 296. The distal loops 293 and 294 of the retention wire 285 act to interlock the side holes 295 and 296 by creating a removable shear pin element which prevents relative axial movement between the distal end 286 of the inflation tube 211 and the inflation port 283. Alternate embodiments may include multiple retention filaments or wires disposed within the lumen 291 of the inflation tube 211. An external sleeve (not shown) may be added over this assembly to further secure the interface and prevent leakage of inflation material through side holes 295 and 296. This sleeve is attached to inflation tube 211 and is received with it.

Figure 14:
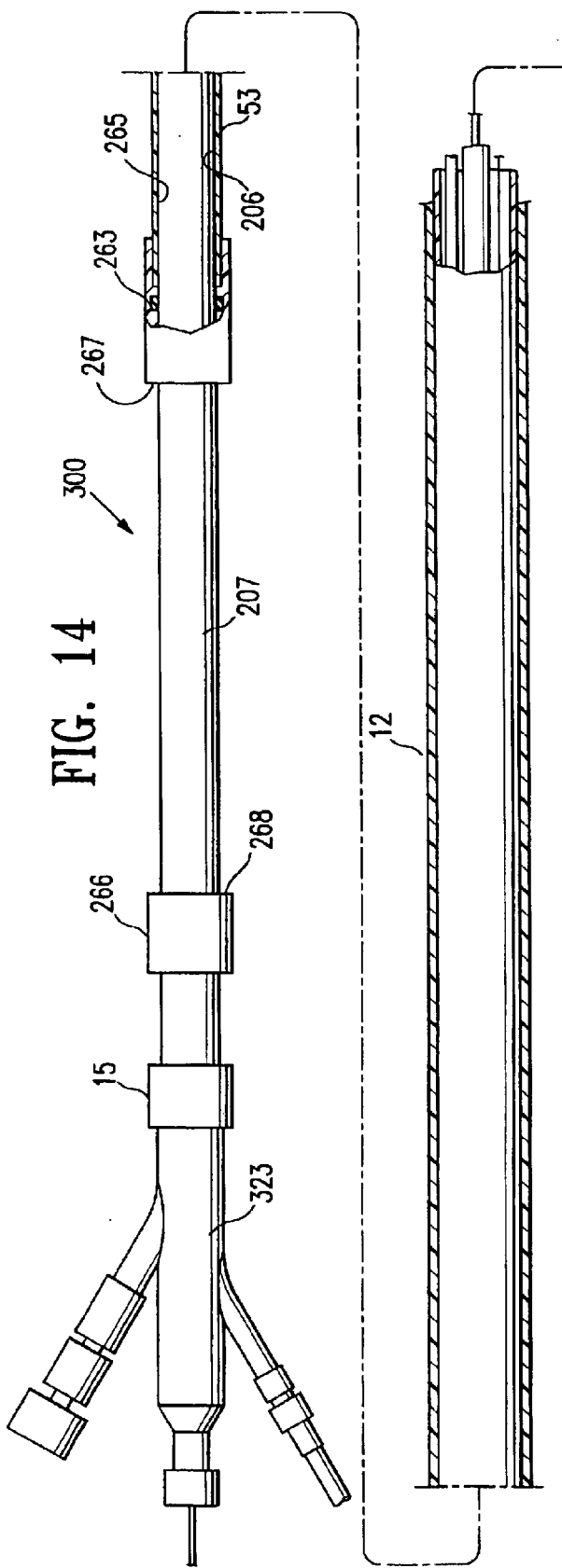
FIG. 14 is an elevational view in partial longitudinal section illustrating an embodiment of a delivery system for an expandable intracorporeal device having features of the invention.
Figure 14:
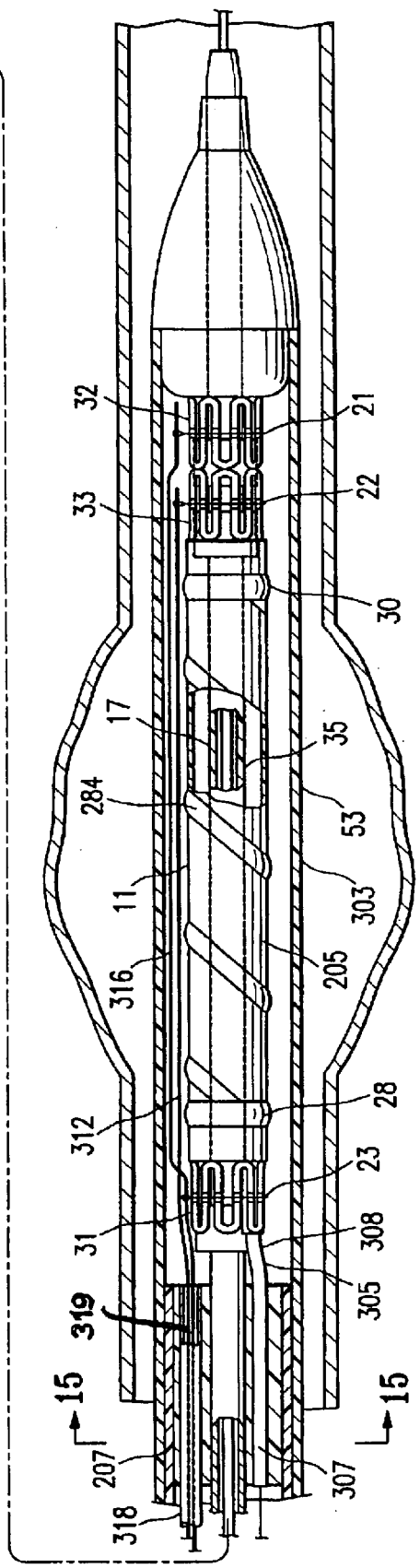
Figure 15:
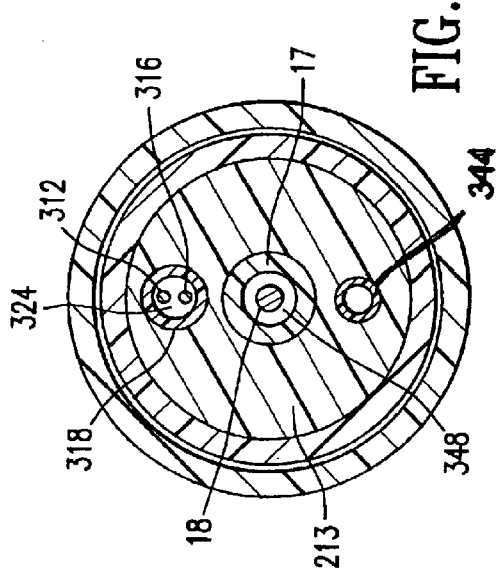
FIG. 15 is a transverse cross sectional view of the delivery system of FIG. 14 taken along lines 15—15 in FIG. 14.
Figure 16:
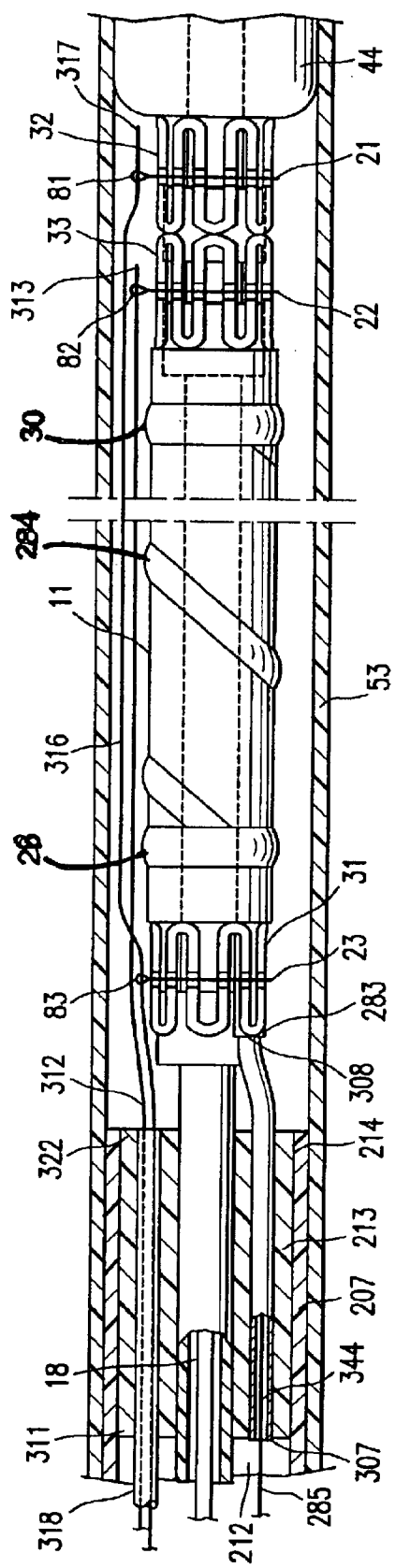
FIG. 16 is an enlarged elevational view in partial section of the delivery system shown in FIG. 14.

FIGS. 14–17 illustrate an alternative embodiment of the delivery system shown in FIG. 1. In FIGS. 14–17, like elements with respect to the embodiment of FIG. 1 will be shown with like reference numerals where appropriate. The delivery system 300 has an outer tubular member 53 and inner tubular member 207 at a distal section 303 of the delivery system 300. An endovascular graft 11 is disposed within the outer tubular member in the distal section 303. An inflation tube 305, similar to that of the embodiment shown in FIG. 1 is coupled to an inflation port 283 of the endovascular graft 11. However, the inflation tube 305, having a proximal end 307 and a distal end 308, does not extend the majority of the length of the delivery system 300. Instead, the proximal end 307 of the inflation tube 305 terminates at a proximal end 311 of the potted section 213 as shown in FIGS. 14–16.

Figure 17:
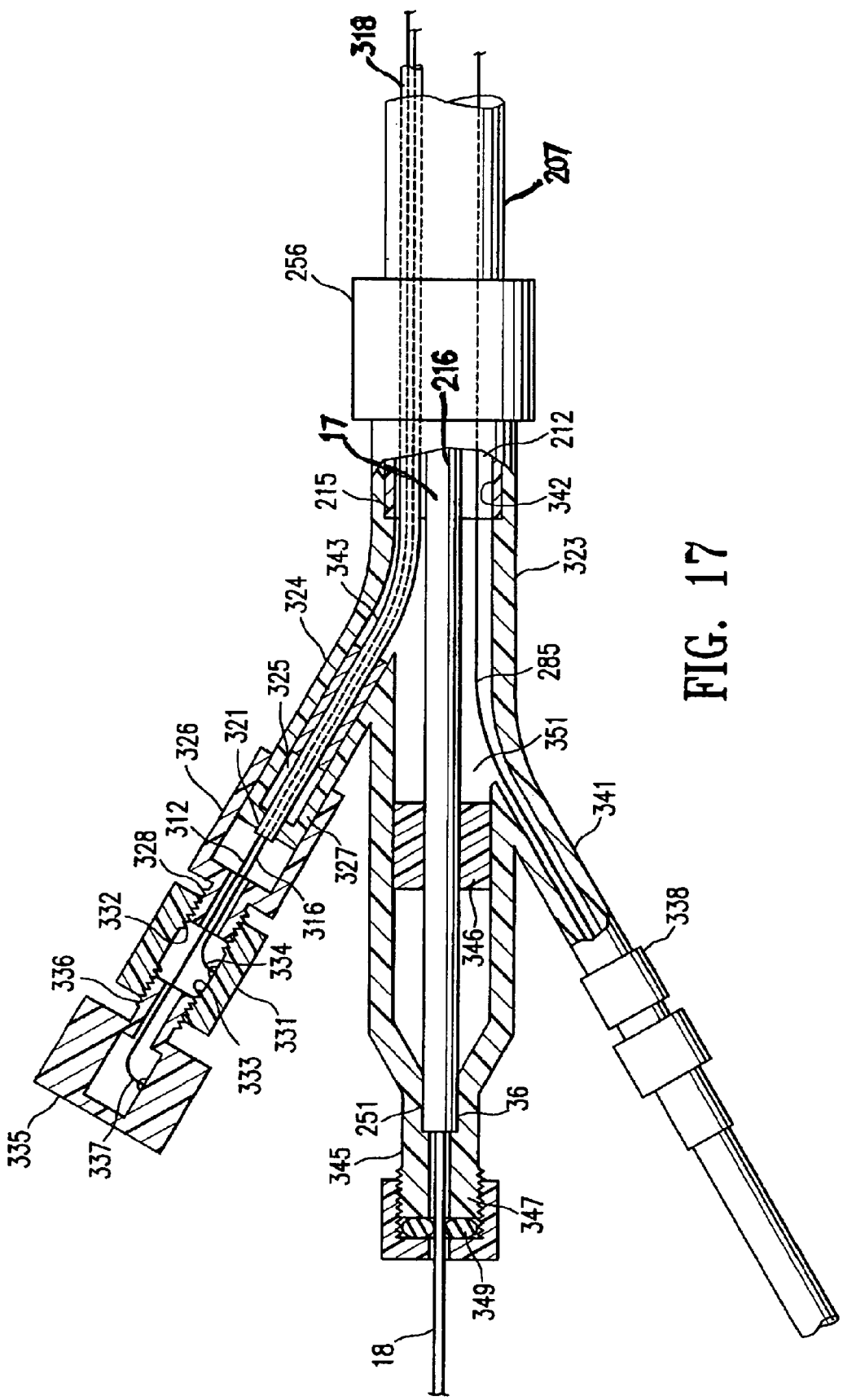
FIG. 17 is an elevational view in partial section of the proximal adapter of the delivery system shown in FIG. 14.

Referring to FIGS. 14 and 16, first release wire 312 having distal end 313 engages end loops 82 of second distal belt 22. The second distal belt 22 is disposed about and constrains the second distal self-expanding member 33. A second release wire 316 having a distal end 317 engages the end loops 81 of the first distal belt 21 and the end loops 83 of the proximal belt 23. The first distal belt 21 is disposed about and constrains the first distal self-expanding member 32. The proximal belt 23 is disposed about and constrains the proximal self-expanding member 31. A release wire tube 318, having a proximal end 321, as shown in FIG. 17, and a distal end 322, shown in FIG. 16, extends from the potted section 213 of the distal section 303 of the delivery system 300 to the proximal adapter 323 shown in FIG. 17. The release wire tube 318 has a lumen 324, as shown in FIG. 15, that contains the first release wire 312 and the second release wire 316.

The proximal adapter 323 has a first side arm 324 with an inner lumen 325 that secures the proximal end 321 of the release wire tube 318. A threaded end cap 326 is secured to a proximal end 327 of the first side arm 324 and has a threaded portion 328. A second release wire handle 331, having a distal threaded portion 332 and a proximal threaded portion 333, is threaded onto the threaded end cap 326. A proximal end 334 of the second release wire 316 is secured to the second release wire handle 331. A first release wire handle 335 has a threaded portion 336 which is releasably threaded onto the proximal threaded portion 333 of the second release wire handle 331. A proximal end 337 of the first release wire 312 is secured to the first release wire handle 335.

Once the outer tubular member 53 has been proximally retracted, belts 21–23 can be released. This configuration allows the operator of the delivery system 300 to first disengage and proximally retract the first release wire handle 335 so as to first release the second distal self-expanding member 33 without releasing or otherwise disturbing the constrained state of the first distal self-expanding member 32 or the proximal self-expanding member 31. Once the second distal self-expanding member 33 has been deployed or released, the endovascular graft 11 may be axially moved or repositioned to allow the operator to adjust the position of the graft 11 for final deployment.

This is advantageous, particularly in the treatment of abdominal aortic aneurysms, because it allows the physician to accurately place graft 11 into position. In many cases, it is desirable for the physician to place the graft 11 such that the distal end of the tubular body portion 205 of the graft is just below the renal arteries 273, shown in FIG. 9, to prevent occlusion of the renal arteries by the tubular body portion 205. If a self-expanding member, such as self-expanding member 32 is radiopaque and the delivery procedure is performed using fluoroscopic imaging, adjustment of the position of the graft after release of self-expanding member is readily achievable. Because self-expanding member 32 is immediately adjacent the distal end of the tubular body portion 205 of the graft 11, the ability to visualize and reposition the self-expanding member 32 is particularly useful in order to position the distal end of the tubular body portion 205 just below the renal arteries without occluding the renal arteries, if such positioning is indicated for the patient being treated.

Thereafter, the second release wire handle 331 may be unscrewed or otherwise released from the end cap 326 and proximally retracted so as to first release the first distal belt end loops 81 and then the proximal belt end loops 83. Of course, the position of the graft 11 may still be adjustable even with both distal self-expanding members 32 and 33 deployed, depending on the particular configuration of the graft 11 and the self-expanding members 32 and 33. The release of the belts 21–23 is the same as that of the belts of the embodiment of FIG. 1 and occurs when the distal end of the release wires 313 and 317 which lock the end loops 81–83 together is proximally retracted past the end loops 81–83 of the belts which are constrained.

Once the self-expanding members 31–33 of the endovascular graft 11 have been deployed or released, and the graft 11 is in a desired location, the graft 11 can then be inflated by injection of an inflation material (not shown) into the injection port 338 on a second side arm 341 of the proximal adapter 323. The inflation material is injected directly into an inner lumen 212 of the inner tubular member 207, as shown in FIG. 17, and travels distally between an inside surface 342 of the inner tubular member 207, outside surface 343 of the release wire tube 318 and outside surface 216 of the guidewire tube 17. This allows the inflation material, which can be highly viscous, to flow through the cross sectional area between the inside surface 342 of the inner tubular member 207 and the outside surfaces 216 and 343 of the release wire tube 318 and guidewire tube 17. This cross sectional area is large relative to the cross sectional area of the inner lumen of the inflation tube 211 of the embodiment of FIG. 1. This results in more rapid flow of inflation material to the inflatable cuffs 28 and 30 and channels 284 of the endovascular graft 11 and decreases inflation time.

Once the inflation material, which is travelling distally in the delivery system 300 during inflation, reaches the potted portion 213 of the distal section 303 of the delivery system, it then enters and flows through a lumen 344, as shown in FIG. 16, at the proximal end 307 of the inflation tube 305 and into the inflation port 283 of the graft 11. Upon inflation of the graft 11 with an inflation material, a release device, such as retention wire 285 can be retracted or otherwise activated so as to de-couple the inflation tube 305 from the inflation port 283 of the endovascular graft 11.

A proximal end 36 of the guidewire tube 17 is secured within a central arm 345 of the proximal adapter 323 which has a potted section 346. A seal 349 is disposed on a proximal end 347 of the central arm 345 for sealing around the guidewire 18 and preventing a backflow of blood around the guidewire. A hemostasis adapter (not shown) can be coupled to the proximal end 347 of the central arm 345 in order to inject fluids through the guidewire tube lumen 348, as shown in FIG. 15, around an outside surface of the guidewire 18. The potted section 346 of the central arm 345 prevents any injected fluids from passing into the inflation material lumen 351 within the proximal adapter 323 or the inner tubular member 207.

Figure 18:
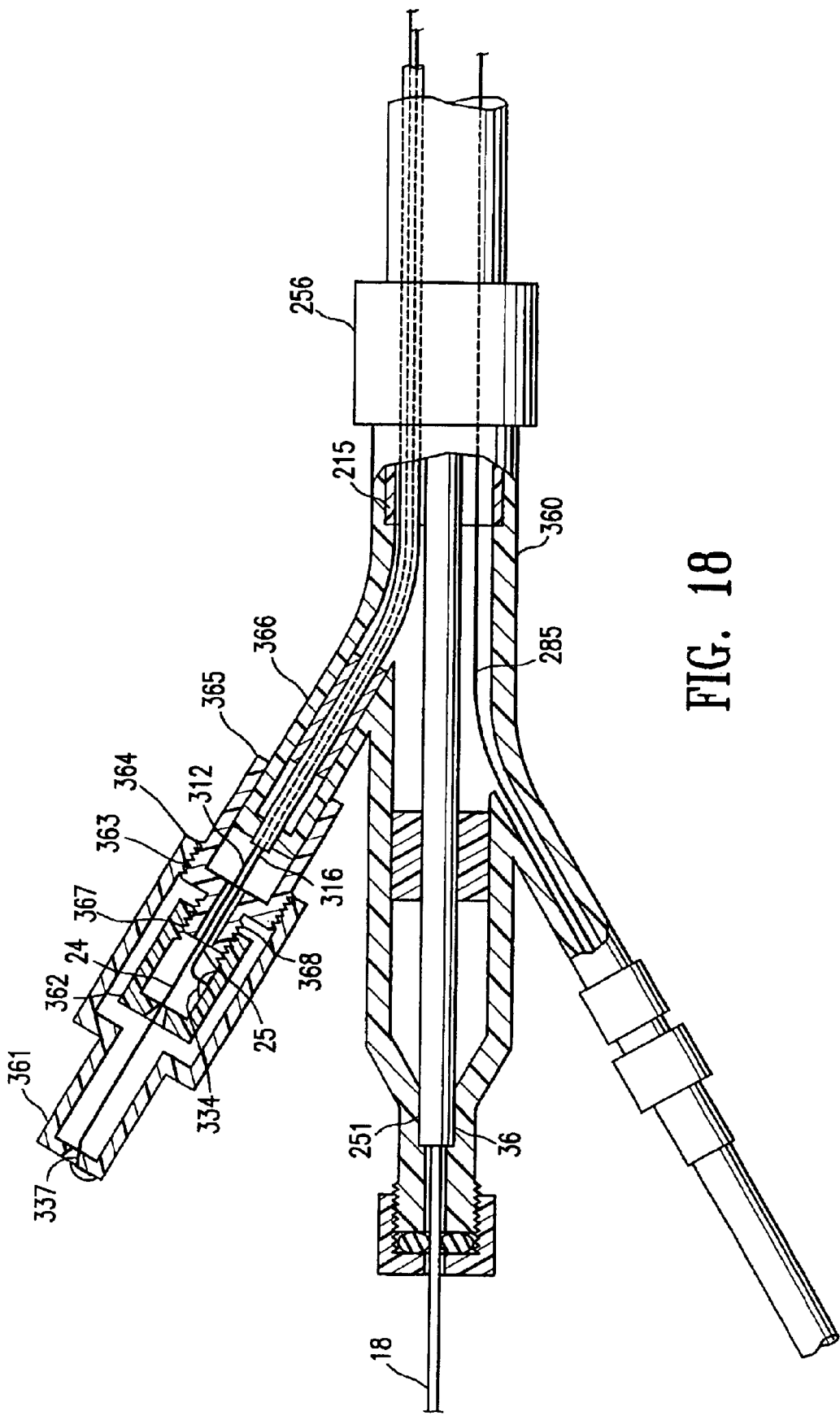
FIG. 18 is an elevational view in partial section of an alternative embodiment of the proximal adapter of the delivery system shown in FIG. 14 with a nested handle configuration.

FIG. 18 illustrates an alternative embodiment to the proximal adapters 42 and 323 used in the embodiments of the invention of FIG. 1 and FIG. 14. In this embodiment, the proximal adapter 360 has a first release wire handle 361 and a second release wire handle 362 which are in a nested configuration. The proximal end 334 of the second release wire 316 is secured to the second release wire handle 362. The proximal end 337 of the first release wire 312 is secured to the first release wire handle 361. This configuration prevents the operator from inadvertently deploying or activating the second release wire 316 prior to deployment or activation of the first release wire 312 which could result in an undesirable endovascular graft deployment sequence.

In use, the operator first unscrews or otherwise detaches a threaded portion 363 of the first release wire handle 361 from an outer threaded portion 364 of a first side arm end cap 365 of a first side arm 366. The first release wire handle 361 is then proximally retracted which releases the end loops 82 of the second distal belt 22 as discussed above with regard to the embodiment of the invention shown in FIG. 14.

Once the first release wire handle 361 is removed from the first side arm end cap 365, the second release wire handle 362 is exposed and accessible to the operator of the delivery system. A threaded portion 367 of the second release wire handle 362 can then be unscrewed or otherwise detached from an inner threaded portion 368 of the first side arm end cap 365. The second release wire handle 362 can then be retracted proximally so as to sequentially deploy the first distal belt 21 and self-expanding member 32 and proximal belt 23 and proximal self-expanding member 31, respectively. The other functions and features of the proximal adapter 360 can be the same or similar to those of the proximal adapters 42 and 323 shown in FIG. 1 and FIG. 17 and discussed above.

While particular forms of the invention have been illustrated and described, it will be apparent that various modifications can be made without departing from the spirit and scope of the invention. Accordingly, it is not intended that the invention be so limited.

What is claimed is:

1. A delivery system for an expandable intracorporeal device comprising:
    an elongate shaft having a proximal section and a distal section with the distal section of the elongate shaft comprising:
        a portion having disposed thereon the expandable intracorporeal device;
        an elongate belt support member disposed within a substantially tubular portion of the expandable intracorporeal device;
        a belt secured to the belt support member and disposed about a circumference of the substantially tubular portion of the expandable intracorporeal device and which constrains at least a portion of the expandable intracorporeal device; and
        a release member which releasably secures the belt in the constraining configuration.

2. The delivery system of claim 1 wherein the belt constrains a self-expanding portion of the expandable intracorporeal device.

3. The delivery system of claim 2 wherein the self-expanding portion is a tubular stent.

4. The delivery system of claim 3 wherein the stent comprises a circumferential groove configured to accept at least a portion of the belt.

5. The delivery system of claim 1 wherein the belt support member is an elongate tubular member and the expandable intracorporeal member is an endovascular graft in a constrained state.

6. The delivery system of claim 1 wherein the belt comprises at least one length of wire having a first end and a second end.

7. The delivery system of claim 6 wherein the at least one length of wire is configured in at least one loop with each of said first and second wire ends secured to the belt support member.

8. The delivery system of claim 6 wherein the wire comprises a shape memory alloy.

9. The delivery system of claim 8 wherein the shape memory alloy comprises nickel titanium.

10. The delivery system of claim 1 wherein the release member comprises a release wire releasably secured to at least one end of the belt.

11. The delivery system of claim 10 wherein the release wire is moveably disposed within opposed looped ends of the belt.

12. The delivery system of claim 1 wherein the belt in the constraining configuration forms a plane which is substantially orthogonal to a longitudinal axis of the elongate shaft.

13. The delivery system of claim 1 wherein a plurality of additional belts are secured to various axial positions on the belt support member and circumferentially disposed about the expandable intracorporeal device and have a configuration that constrains the expandable intracorporeal device, wherein at least one release member releasably secures the belts in the constraining configuration.

14. The delivery system of claim 13 wherein the total number of belts is three.

15. The delivery system of claim 13 wherein at least two belts are configured to be releasable by the same release member.

16. The delivery system of claim 13 wherein all the belts are configured to be releasable by the same release member.

17. The delivery system of claim 15 wherein the order in which the at least two belts are released is determined by the axial position of the at least two belts and the direction of movement of the at least one release member.

18. The delivery system of claim 17 wherein the at least one release member comprises a release wire moveably disposed within opposed looped ends of each belt and wherein the delivery system is configured such that a distal-most belt will be released first when a distal end of the release wire is retracted in a proximal direction so as to move past the looped ends of the distal-most belt, and belts located more proximally are released sequentially thereafter as the distal end of the release wire passes the respective looped ends thereof.

19. A delivery system for an endovascular graft with a flexible tubular body portion and at least one self-expanding member secured to the flexible tubular body portion, comprising:

an elongate shaft having a proximal section and a distal section with the distal section of the elongate shaft comprising:
a portion having disposed thereon the self-expanding endovascular graft;
an elongate belt guidewire tube disposed adjacent the self-expanding member of the endovascular graft;
a belt secured to the belt support member adjacent the self-expanding member and circumferentially disposed about the self-expanding member and which has a configuration which constrains the self-expanding member; and
a release wire releasably securing ends of the belt in the constraining configuration.

20. The delivery system of claim 19 wherein the belt comprises nickel titanium.

21. The delivery system of claim 19 the endovascular graft comprises a plurality of self-expanding members and wherein a plurality of belts are secured to various axial positions on the belt support member adjacent the plurality of self-expanding members, and circumferentially disposed about the self-expanding members and having a configuration which constrains the self-expanding members.

22. The delivery system of claim 21 wherein the release wire is moveably disposed within opposed looped ends of the belts and configured such that a distal-most belt will be released first when a distal end of the release wire is retracted in a proximal direction so as to move past the looped ends of the distal-most belt, and belts located more proximally in an axial direction are released sequentially thereafter as the distal end of the release wire passes the respective looped ends thereof.

23. The delivery system of claim 21 wherein the distal section of the delivery system comprises at least two release wires configured to release different belts.

24. The delivery system of claim 15 wherein the distal section further comprises an outer protective sheath disposed about the endovascular graft while the graft is in a constrained state, the belts being in their constraining configuration and at least a portion of the release wire being disposed at the belts.

25. A delivery system for an endovascular graft with a flexible tubular body portion and a plurality of self-expanding members secured to the tubular body portion, comprising:

an elongate shaft having a proximal section and a distal section with the distal section of the elongate shaft comprising:
a portion having disposed thereon a self-expanding endovascular graft;
an elongate guidewire tube disposed within the endovascular graft with the endovascular graft being in a constrained state;
a plurality of shape memory wire belts secured to the guidewire tube adjacent the respective self-expanding members, the belts being circumferentially disposed about the respective self-expanding members and which have a configuration that constrains the respective self-expanding members;
a first release wire that releasably secures ends of the belts disposed about the self-expanding members at a distal end of the endovascular graft in the constraining configuration; and
a second release wire that releasably secures ends of the belts disposed about the self-expanding members at a proximal end of the endovascular graft in the constraining configuration.

* * * * *